United States Patent [19]
Kuster et al.

[11] Patent Number: 5,634,939
[45] Date of Patent: Jun. 3, 1997

[54] PROGRAM STORAGE DEVICE USABLE WITH A SYSTEM FOR APPLYING LOW ENERGY EMISSION THERAPY

[75] Inventors: Niels Kuster, Zurich; Jean-Pierre Lebet, Montreux; Henry Kunz, Zurich, all of Switzerland; Rea-Woun Chang, Singapore, Singapore; Alexandre Barbault, Colmar, France; Boris Pasche, New York, N.Y.

[73] Assignee: Symtonic, S.A., Switzerland

[21] Appl. No.: 459,399

[22] Filed: Jun. 2, 1995

Related U.S. Application Data

[62] Division of Ser. No. 951,563, Sep. 25, 1992, Pat. No. 5,441,528.
[51] Int. Cl.⁶ ..................................................... A61N 1/32
[52] U.S. Cl. ........................... 607/59; 607/45; 607/69; 607/134; 600/26
[58] Field of Search .............................. 607/2, 45, 46, 607/47, 58, 59, 62, 68, 69, 72, 76, 100, 101, 98, 99, 115, 116, 134; 600/26

[56] References Cited

U.S. PATENT DOCUMENTS

| | | |
|---|---|---|
| 535,905 | 3/1895 | Horton et al. |
| 1,257,555 | 2/1918 | Vreeland . |
| 1,967,815 | 7/1934 | Frieberg . |
| 3,255,753 | 6/1966 | Wing . |
| 3,464,416 | 9/1969 | Williams . |
| 3,762,396 | 10/1973 | Ballentine et al. |
| 3,902,502 | 9/1975 | Liss et al. |
| 4,305,402 | 12/1981 | Katims . |
| 4,312,364 | 1/1982 | Convert et al. ............... 607/98 |
| 4,334,542 | 6/1982 | Takinishi et al. |
| 4,649,935 | 3/1987 | Charmillot et al. |
| 4,765,322 | 8/1988 | Charmillot et al. |
| 4,919,139 | 4/1990 | Brodard ............... 607/69 |
| 4,977,895 | 12/1990 | Tannenbaum . |
| 4,989,605 | 2/1991 | Rossen . |
| 5,002,053 | 3/1991 | Garcia-Rill et al. |
| 5,109,847 | 5/1992 | Liss et al. |
| 5,131,904 | 7/1992 | Markoll . |

FOREIGN PATENT DOCUMENTS

| | | |
|---|---|---|
| 774178 | 12/1967 | Canada . |
| 0 034 516 | 8/1981 | European Pat. Off. |
| 0 469 227 | 2/1992 | European Pat. Off. |
| 1554569 | 12/1968 | France . |
| 305439 | 2/1933 | Italy . |
| WO85/05278 | 12/1985 | WIPO ............... 607/134 |

OTHER PUBLICATIONS

Bawin et al., "Ionic Factors in Release of $^{45}Ca^{2+}$ from Chicken Cerebral Tissue by Electromagnetic Fields," *Proc. Natl. Acad. Si, USA*, vol. 75, No. 12, pp. 6314–6318 (Dec. 1978).

Blackman et al., "Influence of Electromagnetic Fields on the Efflux of Calcium Ions From Brain Tissue In Vitro," *Bioelectromagnetics*, 9:215–227 (1988).

Kaczmarek et al., "The Efflux of $^{45}Ca^{2+}$, and [$^{3H}$]γ-Aminobutyric Acid From Cat cereberal Cortex," *Brain Research*, 63:331–342 (11973).

(List continued on next page.)

*Primary Examiner*—Jeffrey R. Jastrzab
*Attorney, Agent, or Firm*—Arnold, White & Durkee

[57] ABSTRACT

A low energy emission therapy system which includes an emitter of low energy electromagnetic emissions and a probe for applying the emissions to a patient under treatment. The emitter emits a high frequency electromagnetic emission in the form of a carrier signal modulated by a plurality of modulation signals. The invention also includes an impedance transformer located intermediate the emitter and the probe in order to match the impedance of the patient with that of the output of the emitter. Particular modulation signal frequencies and application times and sequences are provided for the treatment of insomnia, and for the treatment of general anxiety disorder which may include panic attacks.

32 Claims, 17 Drawing Sheets

OTHER PUBLICATIONS

Kaczmarek et al., "Weak Electric Gradients Change Ionic and Transmitter Fluxes in Cortex," *Brain Research*, 66:537–540 (1974).

Koella, "The Organization and Regulation of Sleep," *Experientia*, vol. 4, No. 4, pp. 309–408 (Apr. 15, 1984).

Dutta et al., "Microwave Radiation–Induced Calcium Ion Efflux From Human Neuroblastoma Cells in Culture," Bioelectromagnetics 5:71–78 (1984), Alan R. Liss, Inc.

PROGRAM STORAGE DEVICE USABLE WITH A SYSTEM FOR APPLYING LOW ENERGY EMISSION THERAPY

This is a divisional of application Ser. No. 07/951,563, filed Sep. 25, 1992, now U.S. Pat. No. 5,441,528.

BACKGROUND OF THE INVENTION

The invention relates to systems and methods for applying low energy emission therapy for the treatment of central nervous system disorders.

Low energy emission therapy involving application of low energy electromagnetic emissions to a patient has been found to be an effective mode of treating a patient suffering from central nervous system (CNS) disorders such as generalized anxiety disorders, panic disorders, sleep disorders including insomnia, circadian rhythm disorders such as delayed sleep, psychiatric disorders such as depression, obsessive compulsive disorders, disorders resulting from substance abuse, sociopathy, post traumatic stress disorders or other disorders of the central nervous system. Apparatus and methods for carrying out such treatment are described in U.S. Pat. Nos. 4,649,935 and 4,765,322, assigned to the same assignee as the present application, the disclosures of which are expressly incorporated herein by reference. Since the time of these earlier disclosures, a substantially greater understanding of the mechanisms of the treatment and how to secure best results has been gained, which has led to important developments being made to the apparatus (herein described as a system).

Although the apparatus and methods described in the above patents have provided satisfactory results in many cases, consistency and significance of results has sometimes been lacking. Also, it was not always possible to properly control or monitor the duration of treatment or the quantities or nature of the low energy emissions being applied to the patient. Furthermore, the efficiency of transfer of the low energy emissions to the patient was limited and was affected by such factors as patient movement, outside interference and the like.

Another limitation of the previously described apparatus is that it is not very amenable to ready marketing by marketing organizations specifically of the nature comprised in the pharmaceutical industry. The apparatus is intended for therapy or treatment of patients and the low energy emissions applied to the patient are akin to pharmaceutical medication. The marketing organization of a pharmaceutical industry should thus be placed in a position to market the therapy in a fashion not widely different from the fashion in which pharmaceutical products are marketed, e.g., through pharmacists, with or without a doctor's prescription.

Research on treatment for insomnia has lagged behind other medical research programs. Current treatment methods for insomnia consist either of hypnotics, behavioral therapies (e.g. biofeedback), or of the use of drug agents, specifically benzodiazepines or imidazopyridines. Tolerance, dependence, memory loss, and lack of efficacy in long-term treatment are among the most common drawbacks of these classes of currently available hypnotics.

Research throughout the past two decades has shown clearly that the brain serves not only as a communication link and thought-processing organ, but also as the source of significant chemical activity, as well as a number of bioactive compounds. Many of these neurotransmitter compounds and ions are secreted following chemical or electrical stimuli. Research has also shown that some of these neuroactive compounds are involved in the regulation of sleep and wake cycles (Koella, "The Organization and Regulation of Sleep," *Experientia*, 1984; 40(4): 309–408).

During the 1970s, Adey and his group demonstrated that weak electromagnetic fields, modulated at certain well-defined low frequencies, were able to modify the release of ions (calcium) and neurotransmitters (GABA) in the brain (Kaczmarek and Adey, "The Efflux of $^{45}Ca^{2+}$ and [$^{3}H$]γ-aminobutyric Acid from Cat Cerebral Cortex," *Brain Research*, 1973; 63:331–342; Kaczmarek and Adey, "Weak Electronic Gradients Change Ionic and Transmitter Fluxes in Cortex," *Brain Research*, 1974; 66:537–540; Bawin et al., "Ionic Factors in Release of $^{45}Ca^{2+}$ From Chicken Cerebral Tissue by Electromagnetic Fields," Proceedings of the National Academy of Science, 1978; 75(12):6314–6318). In these experiments the cortex of anaesthetized cats was initially incubated with radio-labeled calcium and radio-labeled GABA. When the cortex was exposed to continuous stimulation by weak electric fields modulated at 200 Hz, the researchers found a 1.29-fold increase in Ca++ and a 1.21-fold increase in GABA release (Kaczmarek and Adey, *Brain Research*, 1973; 63:331–342). Interestingly, the release of GABA happened in parallel with the release of Ca++, suggesting that the two phenomena are closely linked. The findings of increased Ca++ release from brain tissue upon stimulation with modulated electromagnetic fields have been replicated (Dutta et al., "Microwave Radiation Induced Calcium Ions Effused from Human Neuroblastoma Cells in Culture," *Bioelectromagnetics*, 1984; 5(1):71–78; and Blackman et al., "Influence of Electromagnetic Fields on the Efflux of Calcium Ions from Brain Tissue in Vitro," *Bioelectromagnetics*, 1988; 9:215–227). It now has become an established fact that weak electric fields modulated at certain low frequencies are able to modulate the release of Ca++ and GABA.

During 1983, it was discovered that weak electromagnetic fields, modulated at low frequencies and delivered by means of an antenna placed in the buccal cavity, caused changes in EEG readings in human volunteers. In agreement with the findings of Adey and Blackman, it was found that only certain well-defined low frequency modulations of a standard carrier frequency (27 MHz), emitted with a well-defined intensity, were capable of eliciting EEG changes.

SUMMARY OF THE INVENTION

The present invention has rendered feasible an entirely new approach to treatment of a patient described in our said earlier patents while avoiding the above-noted drawbacks.

The present invention contemplates provision in the system (apparatus) of an interface for an application storage device, which application storage device can comprise storage media, such as, magnetic storage media, semiconductor memory storage media, optical memory storage media, or mechanical storage media. The selected storage media is programmed to carry various control information. Other information which may be stored in the storage media includes duration control information which would control the duration of the low energy electromagnetic emission and hence the duration of the application of the emission to the patient. Further control information can include duty cycle control information which would control the emissions, for example, in such a fashion that the low energy emission is alternately discontinued and re-initiated for chosen periods of time. Yet further control information which may be programmed into the storage media includes selecting information which would select emissions of various different modulation waveforms and frequencies which emissions can be emitted sequentially, with or without pauses between the emissions. Still further control information that may be programmed into the storage media includes power level control information.

In one embodiment of the invention, the system includes a microprocessor into which is loaded control information from the application storage device. The microprocessor then controls the function of the system to produce the desired therapeutic emission.

Another embodiment of the present invention contemplates that the application storage device would be combined into a single unit, and would be connected to the system through an interface in order to control the system.

In either of these embodiments, the present invention contemplates that the interface may include a communications channel such as, for example, a radio frequency link or telephone line, which connects the application storage device to the rest of the system.

The present invention also contemplates provision in the system of an impedance transformer connected intermediate the emitter of low energy electromagnetic emissions and a probe for applying the emissions to the patient, which impedance transformer substantially matches the impedance of the patient seen from the emitter circuit with the impedance of the output of the emitter circuit.

Another aspect of the present invention is the provision of a power reflectance detector which detects an amount of power applied to a patient and compares that amount to an amount of power emitted by the system. The power detector permits the monitoring of patient compliance with the prescribed treatment. Such patient treatment compliance information may be stored on the application storage device for later retrieval and analysis. For example, the power detector may be used to detect the number of treatments applied to a particular patient, and the elapsed time for each treatment. Further, the actual time of day of each treatment may also be recorded, as may the number of attempted treatments.

These and other features and advantages of the present invention will become apparent to those of skill in this art with reference to the appended drawings and following details description.

DETAILED DESCRIPTION

Figure 1:
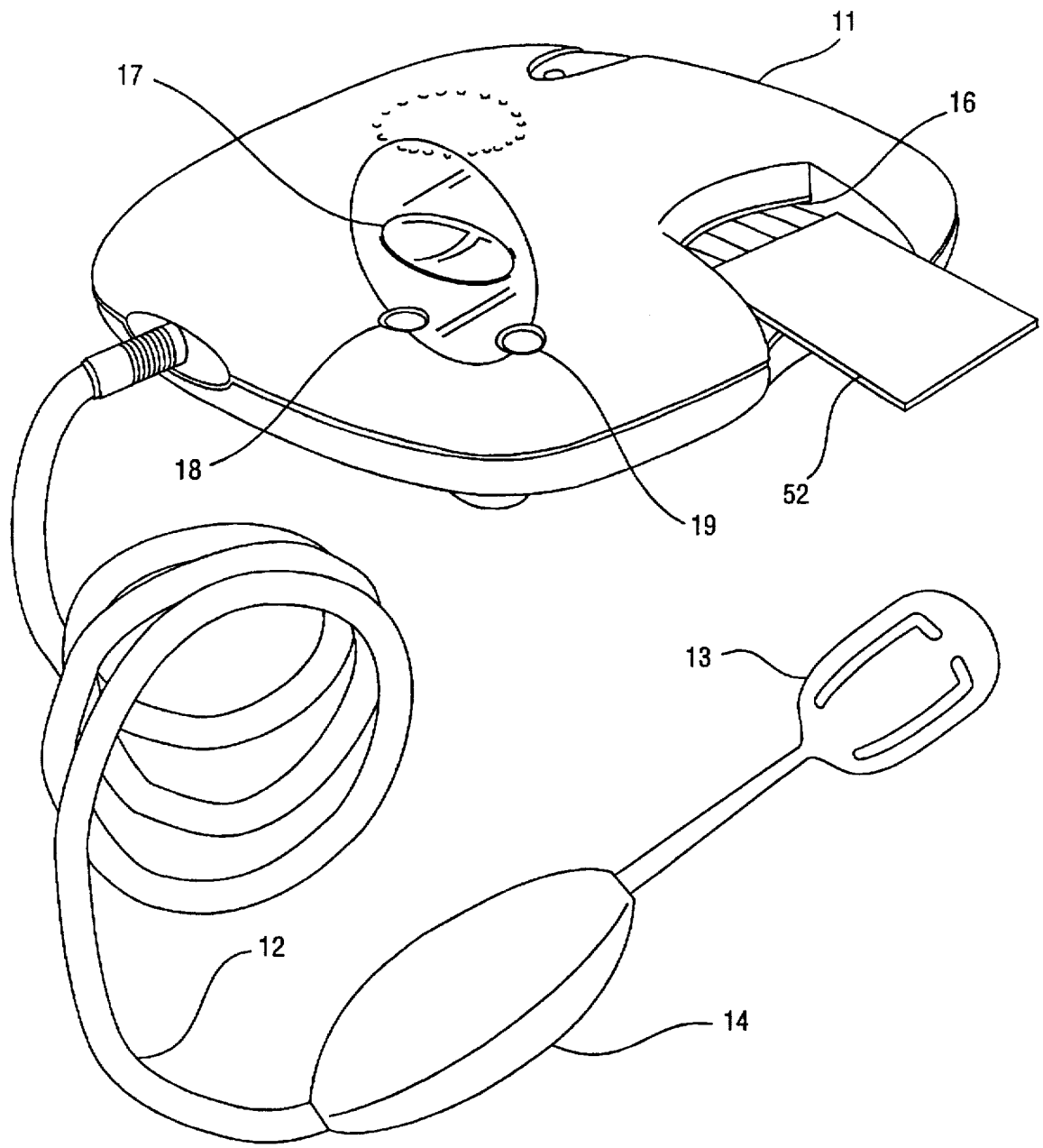
FIG. 1 is a system for applying modulated low energy electromagnetic emission to a patient, in accordance with the present invention.

Referring to FIG. 1, presented is a modulated low energy electromagnetic emission application system 11, in accordance with the present invention. As presented in prior U.S. Pat. Nos. 4,649,935 and 4,765,322, such a system has proven useful in the practice of Low Energy Emission Therapy (LEET, a trademark of the assignee of the present application), which involves application of emissions of low energy radio frequency (RF) electromagnetic waves and which has proven an effective mode of treating a patient suffering from central nervous system (CNS) disorders such as, for example, generalized anxiety disorders, panic disorders, sleep disorders including insomnia, psychiatric disorders such as depression, obsessive compulsive disorders, disorders resulting from substance abuse, sociopathy, post traumatic stress disorders or other disorders of the central nervous system. The system includes a probe or mouthpiece 13 which is inserted into the mouth of a patient under treatment. Probe 13 is connected to an electromagnetic energy emitter (see also FIG. 2), through coaxial cable 12 and impedance matching transformer 14. Although probe 13 is illustrated as a mouthpiece, any probe that is adapted to be applied to any mucosa may be used. For example, oral, nasal, optical, urethral, anal, and/or vaginal probes may be used without departing from the scope of the invention. Probes situated closer to the brain, for example endonasal or oral probes, are presently preferred.

Application system 11 also includes an interface 16 which is adapted to receive an application storage device 52 such as, for example, magnetic media, semiconductor media, optical media or mechanically encoded media, which is programmed with control information used to control the operation of system 11 to apply the desired type of low energy emission therapy to the patient under treatment.

As presented in more detail below, application storage device 52 can be provided with a microprocessor which, when applied to interface 16, operates to control the function of system 11 to apply the desired low energy emission therapy. Alternatively, application storage device 52 can be provided with a microprocessor which is used in combination with microprocessor 21 within system 11. In, such case, the microprocessor within device 52 could assist in the interfacing of storage device 52 with system 11, or could provide security checking functions.

System 11 also includes a display 17 which can display various indications of the operation of system 11. In addition, system 11 includes on and off power buttons 18 and 19.

It will be understood that configurations of application system 11 other than that presented in FIG. 1, may be used without departing from the spirit and scope of the present invention.

Figure 2:
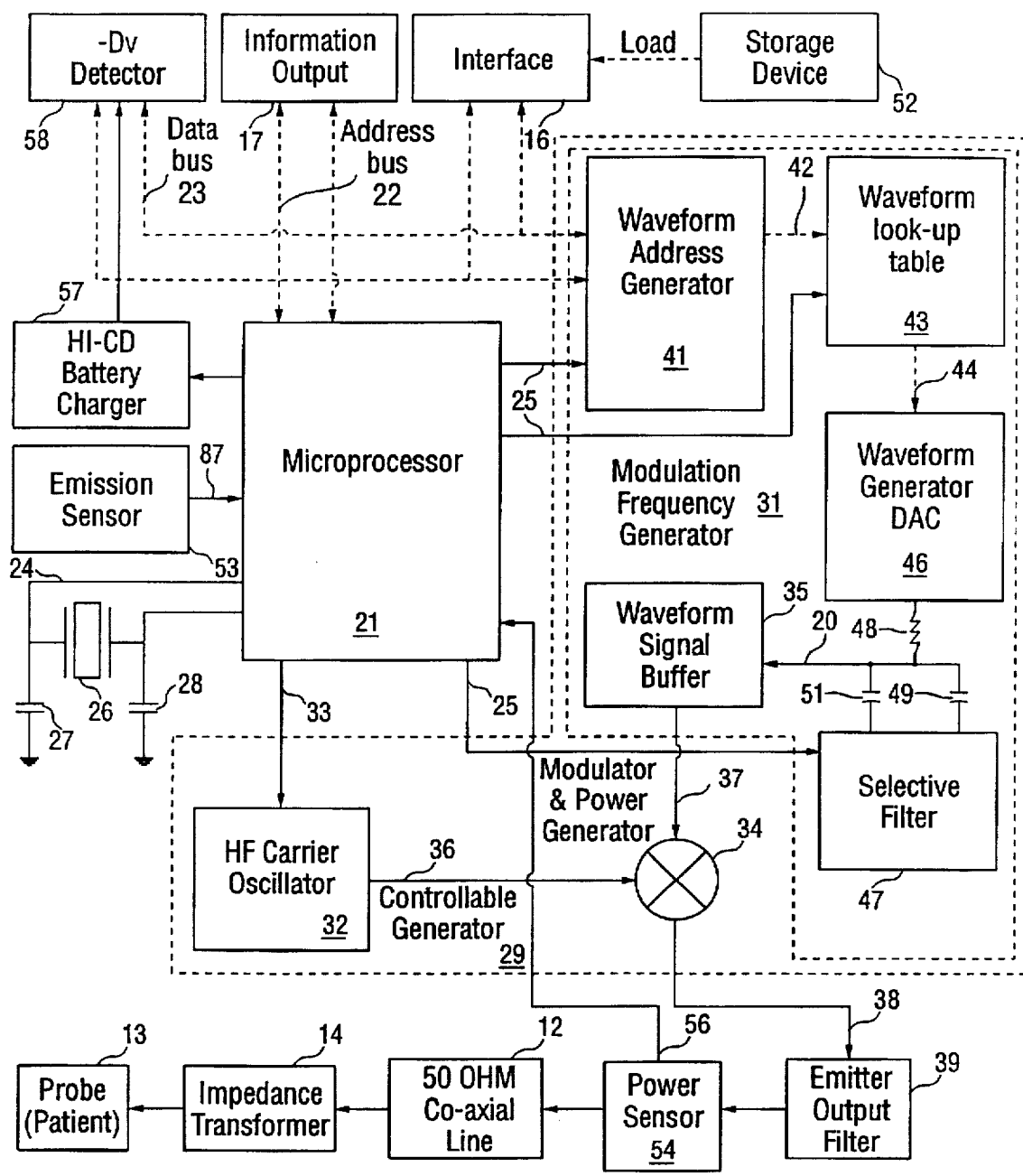
FIG. 2 is a block diagram of the circuitry of the system of FIG. 1.

Referring now to FIG. 2, presented is a block diagram of the electronic circuitry of application system 11, in accordance with the present invention. Microprocessor 21 operates as the controller for application system 11, and is connected to control the various components of the system 11 through address bus 22, data bus 23 and I/O lines 25.

Microprocessor 21 preferably includes internal storage for the operation code, control program, and temporary data. In addition, microprocessor 21 includes input/output ports and internal timers. Microprocessor 21 may be, for example, an 8-bit single-chip micro-controller, 8048 or 8051 available from Intel Corporation The timing for microprocessor 21 is provided by system clock 24 which includes a clock crystal 26 along with capacitors 27 and 28. System clock 24 may run at any clock frequency suitable for the particular type of microprocessor used. In accordance with one embodiment of the present invention, system clock 24 operates at a clock frequency of 8.0 MHz.

The operating program for microprocessor 21 is presented below in flow chart form with reference to FIGS. 11a–d. In general, microprocessor 21 functions to control controllable electromagnetic energy generator circuit 29 to produce a desired form of modulated low energy electromagnetic emission for application to a patient through probe 13.

Controllable generator circuit 29 includes modulation frequency generator circuit 31 and carrier signal oscillator 32. Microprocessor 21 operates to activate or de-activate controllable generator circuit 29 through oscillator disable line 33, as described below in more detail. Controllable generator circuit 29 also includes an AM modulator and power generator 34 which operates to amplitude modulate a carrier signal produced by carrier oscillator 32 on carrier signal line 36, with a modulation signal produced by modulation signal generator circuit 31 on modulation signal line 37.

Modulator 34 produces an amplitude modulated carrier signal on modulated carrier signal line 38, which is then applied to the filter circuit 39. The filter circuit 39 is connected to probe 13 via coaxial cable 12 and impedance transformer 14.

Microprocessor 21 controls modulation signal generator circuit 31 of controllable generator circuit 29 through address bus 22, data bus 23 and I/O lines 25. In particular, microprocessor 21 selects the desired waveform stored in modulation waveform storage device 43 via I/O lines 25. Microprocessor 21 also controls waveform address generator 41 to produce on waveform address bus 42 a sequence of addresses which are applied to modulation signal storage device 43 in order to retrieve the selected modulation signal. The desired modulation signal is retrieved from modulation signal storage device 43 and applied to modulation signal bus 44 in digital form. Modulation signal bus 44 is applied to digital to analog converter (DAC) 46 which converts the digital modulation signal into analog form. This analog modulation signal is then applied to selective filter 47 which, under control of microprocessor 21, filters the analog modulation signal by use of a variable filter network including resistor 48 and capacitors 49 and 51 in order to smooth the wave form produced by DAC 46 on modulation signal line 20.

In the present embodiment, the various modulation signal wave forms are stored in modulation signal storage device 43. With a 2 kilobyte memory, storage device 43 can contain up to 8 different modulation signal wave forms. Wave forms that have been successfully employed include square wave forms or sinusoidal wave forms. Other possible modulation signal wave forms include rectified sinusoidal, triangular, and combinations of all of the above.

In the present embodiment, each modulation signal wave form uses 256 bytes of memory and is retrieved from modulation signal storage device 43 by running through the 256 consecutive addresses. The frequency of the modulation signal is controlled by how fast the wave form is retrieved from modulation signal storage device 43. In accordance with the present embodiment, this is accomplished by downloading a control code from microprocessor 21 into programmable counters contained within wave form address generator 41. The output of the programmable counters then drives a ripple counter that generates the sequence of 8-bit addresses on the wave form address bus 42.

Wave form address generator 41 may be, for example, a programmable timer/counter uPD65042C, available from NEC. Modulation signal storage device 43 may be, for example, a type 28C16 Electrical Erasable Programmable Read Only Memory (EEPROM) programmed with the desired wave form table. Digital to analog converter 46 may be, for example, a DAC port, AD557JN available from Analog Devices, and selective filter 47 may be a type 4052 multiplexer, available from National Semiconductor or Harris Semiconductor.

The particular modulation control information used by microprocessor 21 to control the operation of controllable generator circuit 29, in accordance 7ith the present invention, is stored in application storage device 52. As presented below in more detail with reference to FIGS. 12, 13, 14 and 15, application storage device 52 may be any storage device capable of storing information for later retrieval. For example, application storage device 52 may be, for example, a magnetic media based storage device such as a card, tape, disk, or drum. Alternatively, application storage device 52 may be a semiconductor memory-based storage device such as an erasable programmable read only memory (EPROM), an electrical erasable programmable read only memory (EEPROM) or a non-volatile random access memory (RAM). Another alternative for application storage device 52 is a mechanical information storage device such as a punched card, cam, or the like. Yet another alternative for application storage device 52 is an optical storage device such as a compact disk read only memory (CD ROM).

It should be emphasized that although the figures illustrate microprocessor 21 separate from application storage device 52, microprocessor 21 and application storage device 52 may both be incorporated into a single device, which is loaded into system 11 to control the operation of system 11 as described herein. In this case, interface 16 would exist between the combination of microprocessor 21 and application storage device 52 and the rest of system 11.

Interface 16 is configured as appropriate for the particular application storage device 52 in use. Interface 16 translates the control information stored in application storage device 52 into, a usable form for storage within the memory of microprocessor 21 to enable, microprocessor 21 to control controllable generator circuit 29 to produce the desired modulated low energy emission.

Interface 16 may directly read the information stored on application storage device 52, or it may read the information through use of various known communications links. For example, radio frequency, microwave, telephone or optical based communications links may be used to transfer information between interface 16 and application storage device 52.

When application storage device 52 and microprocessor 21 are incorporated in the same device, interface 16 is configured to connect microprocessor 21 to the rest of system 11.

The control information stored in application storage device 52 specifies various controllable parameters of the modulated low energy RF electromagnetic emission which is applied to a patient through probe 13. Such controllable parameters include, for example, the frequency and amplitude of the carrier, the amplitudes and frequencies of the modulation of the carrier, the duration of the emission, the power level of the emission, the duty cycle of the emission (i.e., the ratio of on time to off time of pulsed emissions applied during an application), the sequence of application of different modulation frequencies for a particular application, and the total number of treatments and duration of each treatment prescribed for a particular patient.

For example, the carrier signal and modulation signal may be selected to drive the probe 13 with an amplitude modulated signal in which the carrier signal includes spectral frequency components below 1 GHz, and preferably between 1 MHz and 900 Mhz, and in which the modulation signal comprises spectral frequency components between 0.1 Hz and 10 KHz, and preferably between 1 Hz and 1000 Hz. In accordance with the present invention, one or more modulation frequencies may be sequenced to form the modulation signal.

As an additional feature, an electromagnetic emission sensor 53 may be provided to detect the presence of electromagnetic emissions at the frequency of the carrier oscillator 32. Emission sensor 53 provides to microprocessor 21 an indication of whether or not electromagnetic emission at the desired frequency are present. As described below in more detail, microprocessor 21 then takes appropriate action, for example, displaying an error message on display 17, disabling controllable generator circuit 29, or the like.

The invention also includes a power sensor 54 which detects the amount of power applied to the patient through probe 13 compared to the amount of power returned or reflected from the patient. This ratio is indicative of the proper use of the system during a therapeutic session. Power sensor 54 applies to microprocessor 21 through power sense line 56 an indication of the amount of power applied to patient through probe 13 relative to the amount of power reflected from the patient.

The indication provided on power sense line 56 may be digitized and used by microprocessor 21, for example, to detect and control a level of applied power, and to record on application storage device 52 information related to the actual treatments applied. Such information may then be used by a physician or other clinician to assess patient treatment compliance and effect. Such treatment information may include, for example: the number of treatments applied for a given time period; the actual time and date of each treatment; the number of attempted treatments; the treatment compliance (i.e., whether the probe was in place or not in place during the treatment session); and the cumulative dose of a particular modulation frequency.

The level of power applied is preferably controlled to cause the specific absorption rate (SAR) of energy absorbed by the patient to be from 1 microWatt per kilogram of tissue to 50 Watts per kilogram of tissue. Preferably, the power level is controlled to cause an SAR of from 100 microWatts per kilogram of tissue to 10 Watts per kilogram of tissue. Most preferably, the power level is controlled to cause an SAR of from 1 milliWatt per kilogram of tissue to 100 milliWatts per kilogram of tissue. These SARs may be in any tissue of the patient, but are preferably in the tissue of the central nervous system.

System 11 also includes powering circuitry including battery and charger circuit 57 and battery voltage change detector 58.

FIGS. 3–10 present in more detail various components of the system of FIG. 2.

Figure 3:
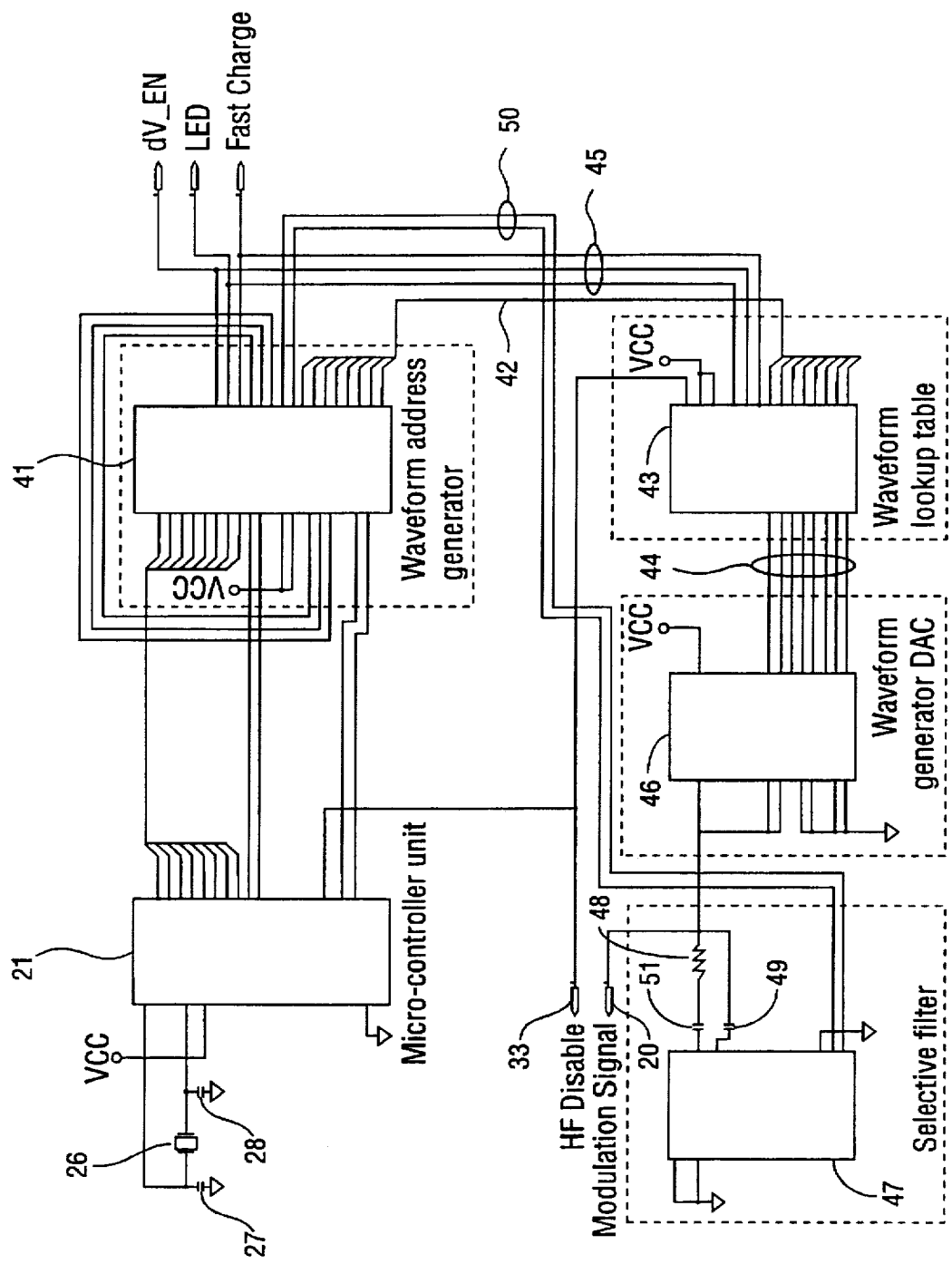
FIG. 3 is a detailed schematic of the modulation signal generator of the circuit of FIG. 2.

Referring first to FIG. 3, presented is a detailed schematic of controllable modulation frequency generator 31. Modulation frequency generator 31 includes wave form address generator 41, modulation signal storage device 43, digital to analog converter 46 and a selective filter network 47.

Microprocessor 21 controls extended I/O lines 45 and selects the desired wave form from wave form storage device 43. Microprocessor 21 then downloads the control information to the wave form address generator 41 which in turn generates a sequence of the wave form addresses. The sequence of addresses are then applied to the modulation signal storage device 43 through address bus 42. The desired modulation signal is then retrieved from the storage device 43 and appears on signal bus 44 in digital form. After a digital to analog conversion by the digital to analog converter 46, the modulation signal is filtered and is output onto the modulation signal line 20.

The frequency of the modulation signal is determined by the rate at which the sequence of wave form addresses is generated. The type of modulation signal is selected by microprocessor 21 via extended I/O lines 45 and the filtering network is selected via I/O line 50.

Figure 4:
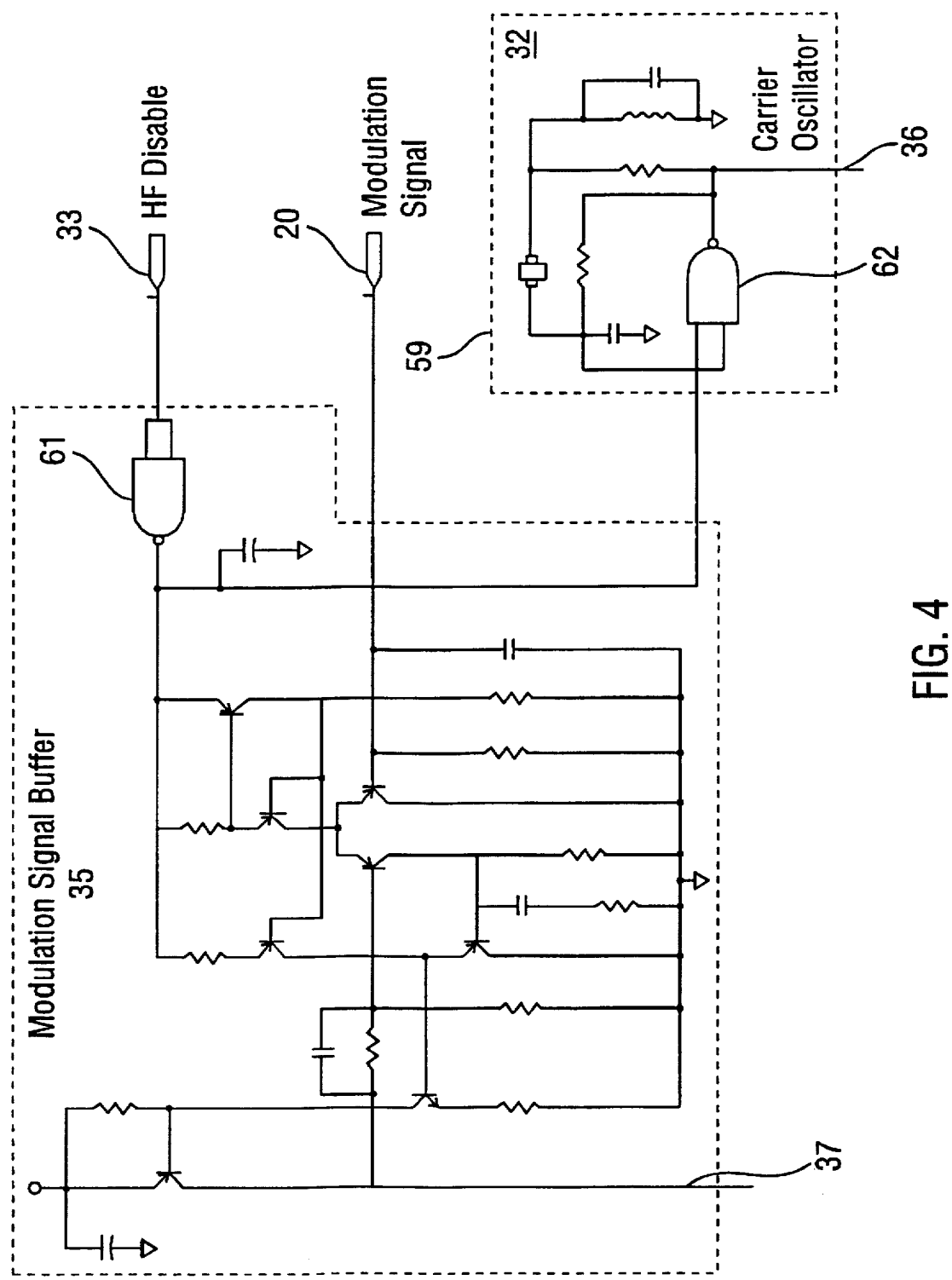
FIG. 4 is a detailed schematic of the modulation signal buffer and the carrier oscillator circuit used in the circuit of FIG. 2.

Referring now to FIG. 4, presented is a detailed schematic of the modulation signal buffer amplifier 35 and the carrier frequency oscillator circuit 32.

The modulation signal buffer amplifier 35 is basically a non-inverting amplifier in discrete form. The amplifier buffers the modulation signal 20 from the selective filter 47 and provides necessary modulation signal amplitude and current drive to the AM modulator and power generator circuit 34. The output stage is designed in such a way that the output signal 37 achieves a rail-to-rail voltage swing. The output of the modulation signal buffer appears on signal line 37.

It should be noted that although the disclosed embodiment contemplates that the gain of modulation signal buffer amplifier 35 is substantially constant, the invention also contemplates use of a variable gain amplifier that is controlled by microprocessor 21 in order to vary the magnitude of the modulation signal on line 37, thus permitting programmable control of the level of power applied.

The carrier oscillator 32 is constructed around carrier oscillator crystal 59. In one embodiment, carrier oscillator 32 produces a Radio Frequency (RF) carrier frequency of 27 MHz. Other embodiments of the invention contemplate RF carrier frequencies of 48 MHz, 450 MHz or 900 MHz. In general, the RF carrier frequency produced by carrier oscillator 32 has spectral frequency components less than 1 GHz and preferably between 1 MHz and 900 MHz. It should also be noted that while the disclosed embodiment contemplates that once set, the carrier oscillator frequency remains substantially constant, the present invention also contemplates that carrier frequency produced by carrier oscillator 32 is variable and controllable by microprocessor 21 by use of control information stored on application storage device 52. This would be accomplished, for example, by use of high frequency oscillator, the output of which is conditioned by a controllable clock divider circuit to produce a controlled carrier frequency signal.

Carrier oscillator 32 produces on carrier signal line 36 a carrier signal which is to be modulated by the modulation signal carried on signal line 37.

Oscillator disable line 33 is applied to NAND gate 61, the output of which is applied to NAND gate 62. This configuration allows microprocessor 21 to disable both modulation signal buffer 35 and carrier oscillator 32 by applying an appropriate disable signal to oscillator disable line 33.

Figure 5:
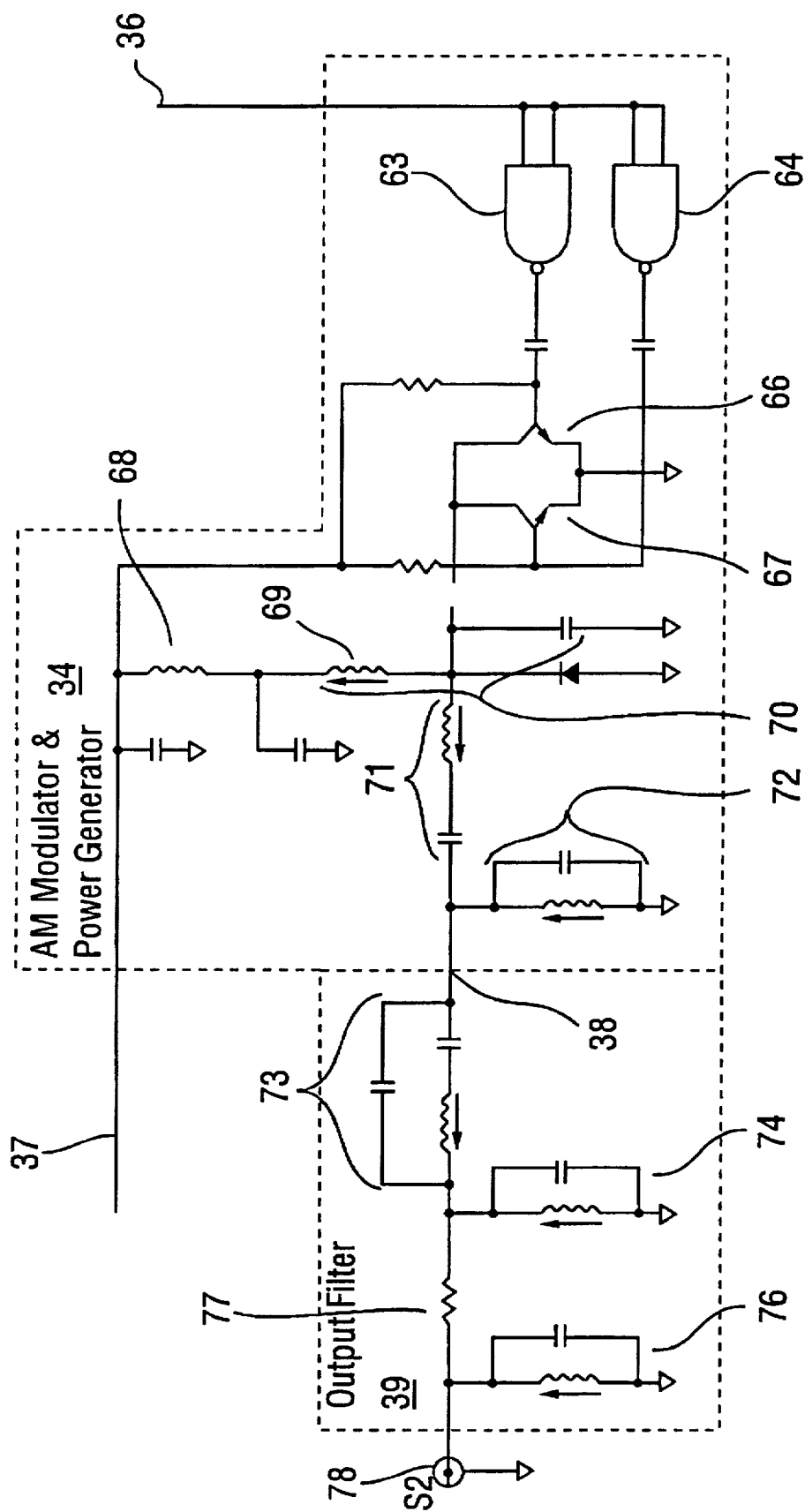
FIG. 5 is a detailed schematic of the AM modulation and power generator and output filter of the circuit of FIG. 2.

FIG. 5 presents a detailed schematic of the AM modulator and power generator 34 and the output filter 39. The AM modulator is made up of two transistors 66 and 67 connected in parallel and operated in zero-crossing switching mode. The carrier signal 36 is applied at the bases of the transistors 66 and 67 through NAND gates 63 and 64, and the modulation signal 37 is applied to the collectors of transistors 66 and 67 through inductors 68 and 69. The net result is the modulated carrier that appears at the collectors of the transistors 66 and 67.

The output power is generated by a single-ended tuned resonant converters configured by three pairs of inductors and capacitors, 70, 71 and 72. LC resonant circuits 70, 71 and 72 are tuned to provide the required output power and are optimized to the maximum efficiency of the converter.

The output of the AM modulator and power generator 34 appears on signal line 38. This modulated signal is applied through output filter network 39 to output connector 78. Output filter 39 included three LC filtering stages, 73, 74 and 76.

The first LC filtering stage, 73 is a band-pass and band-notch filter with pass band centered at 27 MHz and band notch centered at 54 MHz. The band-notch filter provides additional suppression to the second harmonic of the carrier. The second and third LC filtering stages 74 and 76 are both band pass filters which have pass band centered at 27 MHz. The three stage output filter serves to substantially eliminate the carrier harmonics that result from zero-crossing switching of the AM modulator circuit 34.

The output series resistor 77 is used to adjust the output impedance of the modulator. It is found from measurement that the output impedance of the AM modulator is considerably lower than 50 ohm. The series resistor 77 adjusts the output impedance of the circuit is approximately 50 ohms.

Figure 6:
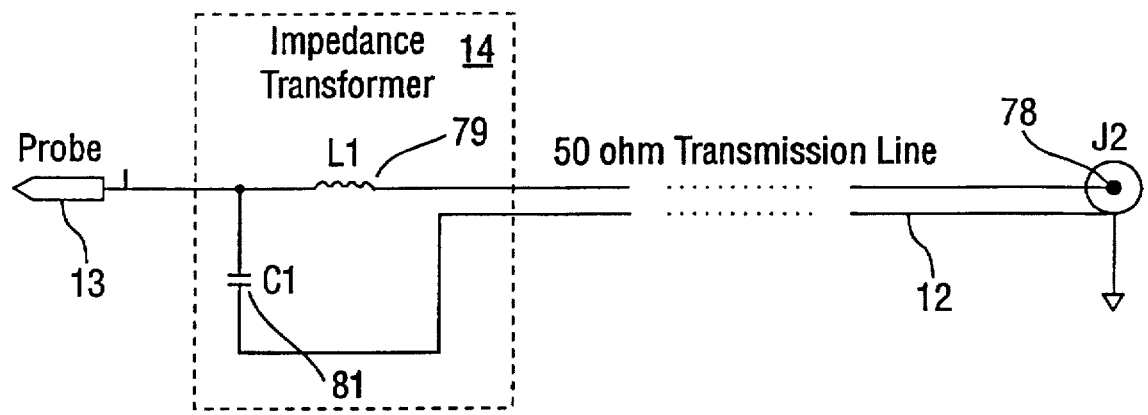
FIG. 6 is a detailed schematic of the impedance transformer of the circuit of FIG. 2.

FIG. 6 presents the details of the impedance transformer 14. Referring also to FIGS. 1, 2, and 5, the output of the AM modulator and power generator 34 and filter stage 39 is designed to have a 50 Ohm output impedance which is chosen to match the 50 Ohm impedance of coaxial cable 12. Impedance transformer 14 includes inductor 79 connected between probe 13 and the middle conductor of coaxial cable 12, and a capacitor 81 connected between probe 13 and the ground conductor of coaxial cable 12.

It has been determined through impedance measurements that when probe 13 is applied to the mouth of a patient, the probe/patient combination exhibits a complex impedance on the order of 150+j200 Ohms. Impedance transformer 14 serves to match this complex impedance with the 50 Ohm impedance of coaxial cable 12 and therefore the output impedance of the AM modulator 34 and output filter 39. This promotes power transmission, and minimizes reflections. In one embodiment, inductor 79 is 0.68 microHenry, and capacitor 81 is 47 picoFarads.

Figure 7:
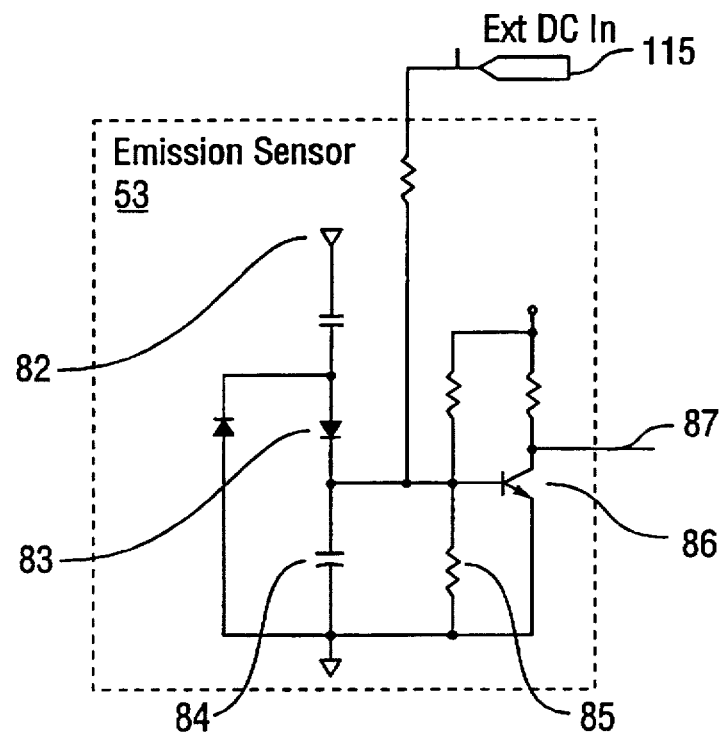
FIG. 7 is a detailed schematic of the emission sensor circuit of the circuit of FIG. 2.

FIG. 7 presents the detailed schematic of the emission sensor 53 of the present invention. Emission sensor 53 includes antenna 82 which is capable of detecting electromagnetic fields at the frequency of the carrier oscillator 32. The signal induced by antenna 82 is applied to a simple diode detector formed by diode 83, capacitor 84 and resistor 85. The demodulated low frequency signal is then applied to the base of a transistor 86 operating as a switch. The output is a low level signal line 87 which is connected to microprocessor 21. Emission sensor 53 is used at the beginning of a treatment session to detect whether probe 13 is emitting electromagnetic fields of the carrier frequency. If so, microprocessor 21 produces on display 17 an indication that the proper electromagnetic field is being produced.

Figure 10:
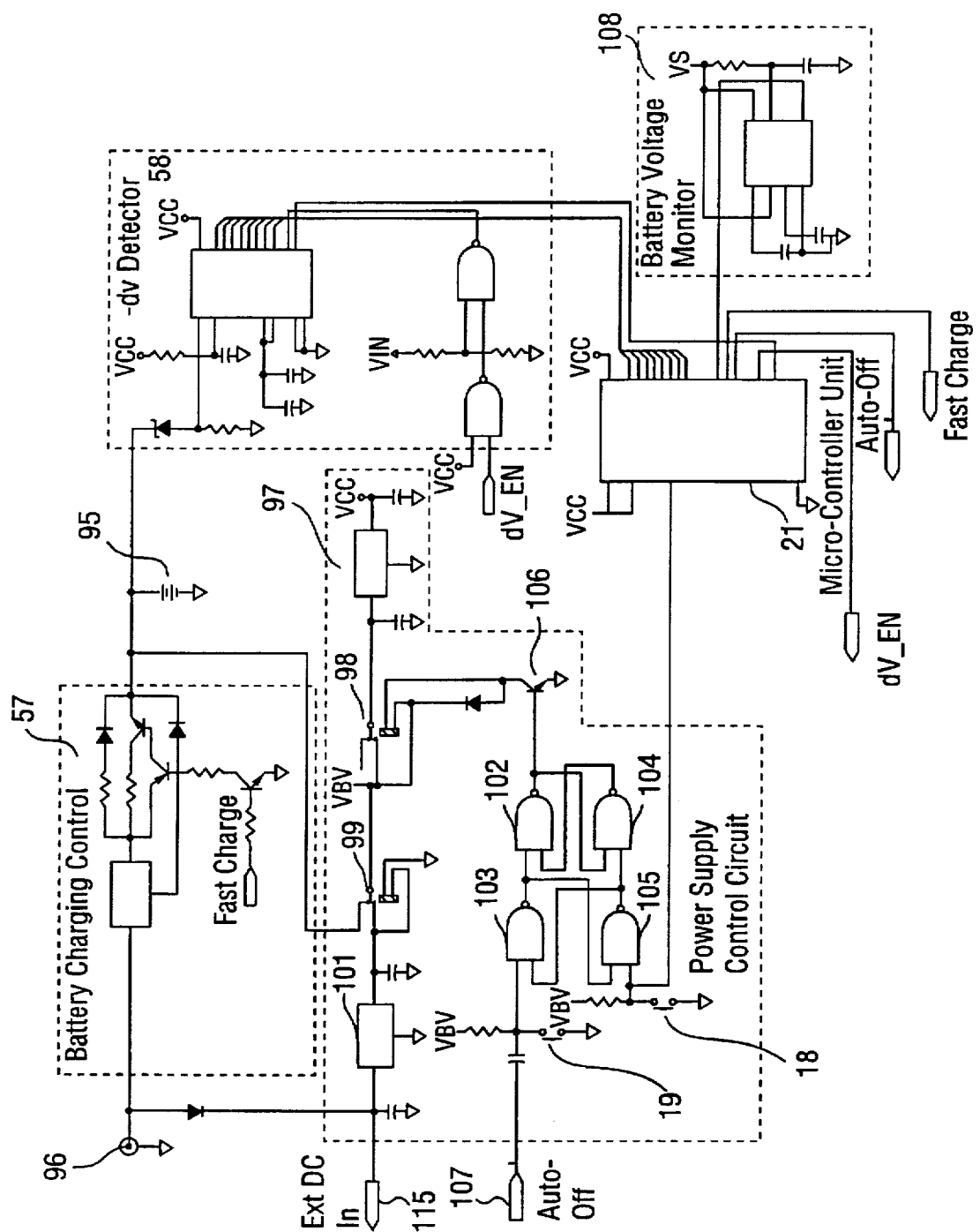
FIG. 10 is a detailed schematic of the power supply circuit used in the circuit of FIG. 2.

Emission sensor 53 is also connected to the power supply circuitry through EXT DC IN line 115 (see also, FIG. 10). When external dc power is applied, line 115, which is connected to the base of transistor 86, turns transistor 86 on, thus providing an indication to microprocessor 21 that external dc power is applied.

Figure 8:
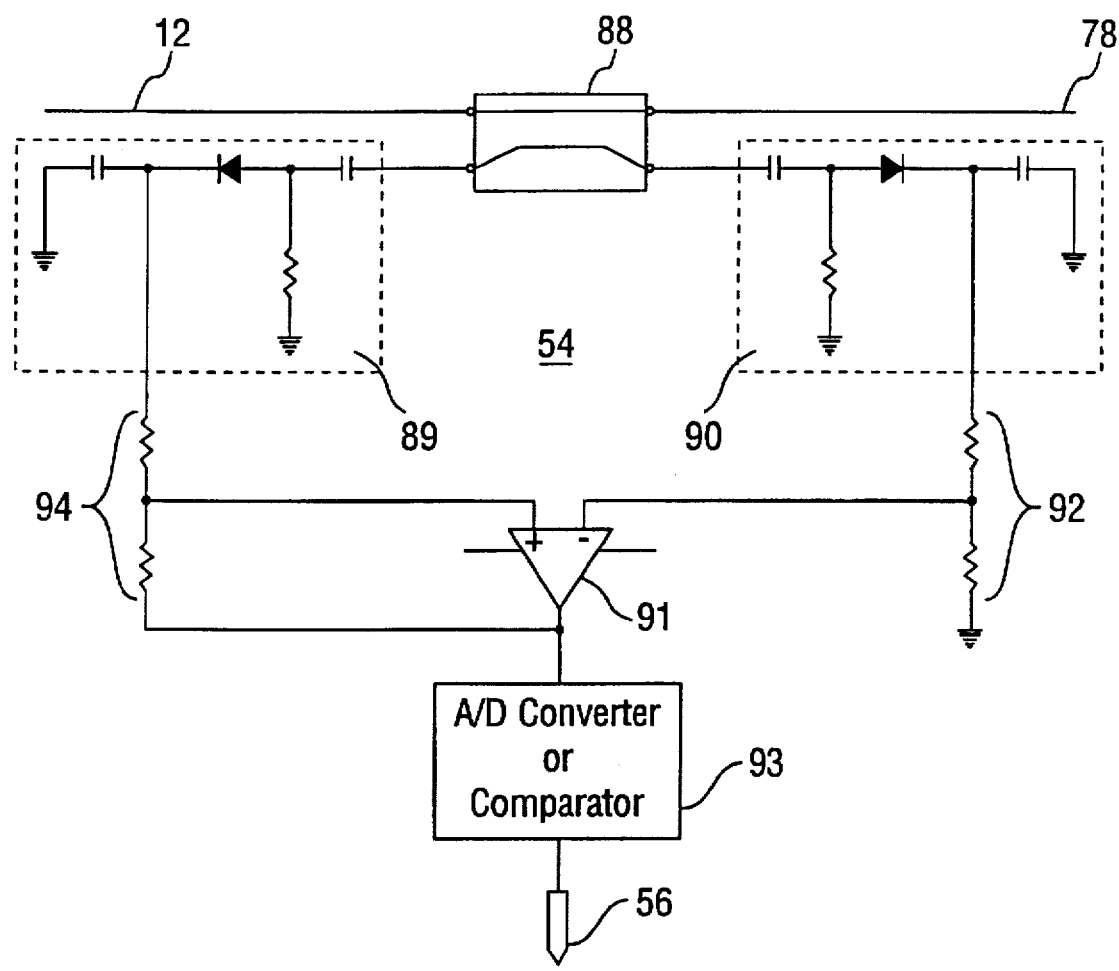
FIG. 8 is a detailed schematic of the output power sensor circuit used in the circuit of FIG. 2.

Referring now to FIG. 8, presented is a schematic of the power sensor 54 used to sense the ratio of the power applied to the patient through probe 13 to the power reflected from to the patient. This ratio is indicative of the efficiency of power transfer from the application system 11 to the patient, and may be used to assess patient treatment compliance. Power sensor 54 may also be used to monitor the level of power being applied to the patient.

Power sensor 54 includes bi-directional coupler 88 which can be, for example, a model KDP-243 bi-directional coupler available from Synergy Microwave Corporation. Bi-directional coupler 88 operates to couple a portion of the energy emitted by application system 11 through output connected 78 and carried by coaxial cable 12 into detecting circuits 89 and 90.

Output connector 78 is connected to a primary input of bi-directional coupler 88 and co-axial cable 12 is connected to a primary output of bi-directional coupler 88. Bi-directional coupler 88 includes two secondary outputs, each of which are connected to respective detecting circuits 89 and 90. Detecting circuit 89 functions to detect the amount of power applied to the patient, and detecting circuit 90 functions to detect the amount of power reflected from the patient. Detecting circuit 89 is connected through resistive divider 94 to the positive input of differential amplifier 91. Detecting circuit 90 is connected through resistive divider 92 to the negative input of differential amplifier 91. The output of differential amplifier 91 is indicative of the difference between the power transmitted to the patient by application system 11, and the power reflected from the patient, and thus is indicative of an amount of power absorbed by the patient. The output of differential amplifier 91 is applied to an analog to digital converter (ADC) or comparator 93, the output of which connected to microprocessor 21 through power sense line 56.

As described in more detail below with reference to the flow chart of FIGS. 11a–d, microprocessor 21 operates to analyze the signal appearing on power sense line 56 to determine and control the amount of power applied to the patient, and to assess patient treatment compliance, and possibly to record indicia of the patient treatment compliance on application storage device 52 for later analysis and assessment by a physician or other clinician.

Figure 9:
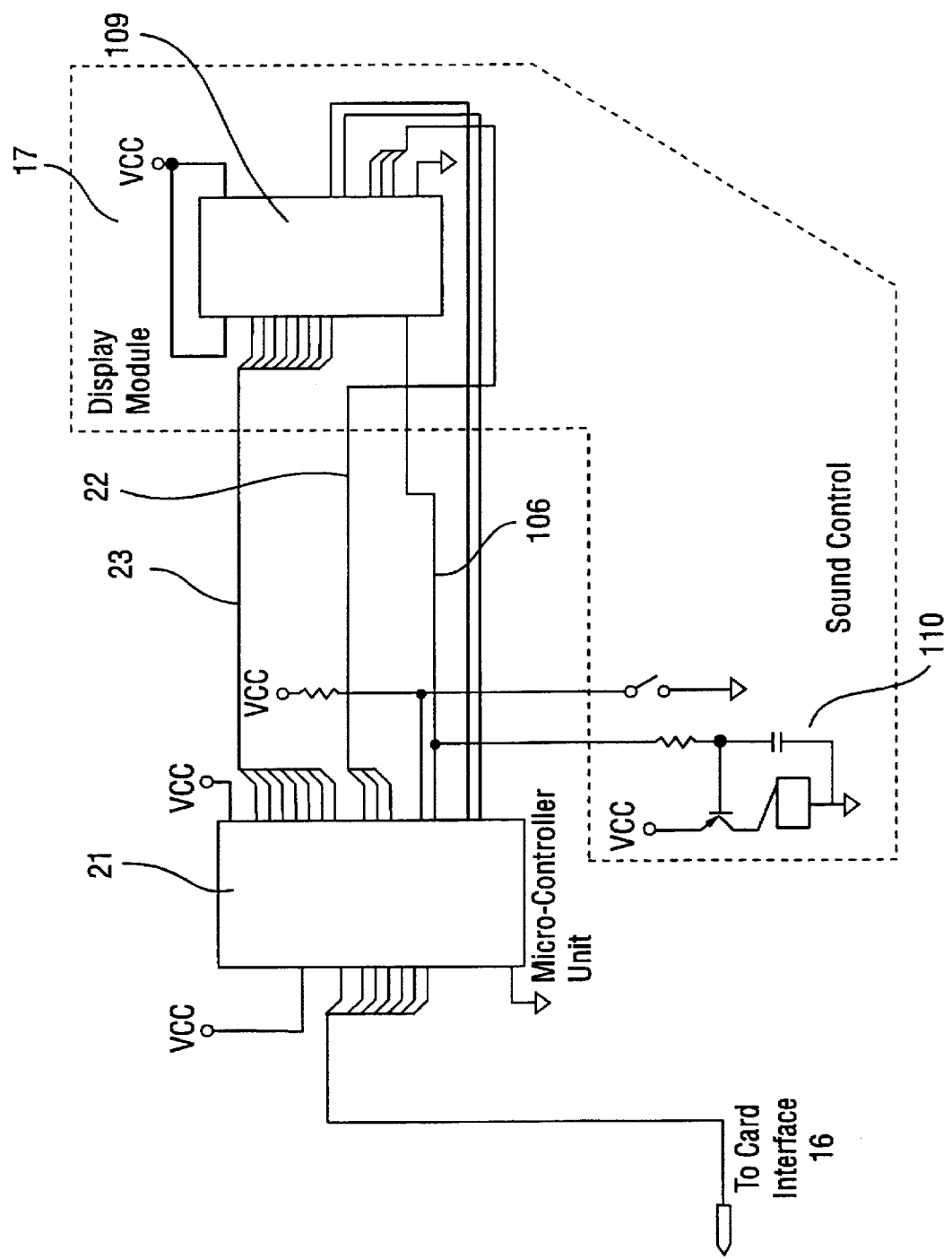
FIG. 9 is a detailed schematic of the display module used in the circuit of FIG. 2.

FIG. 9 presents a detailed schematic of the information output circuit 17. Microprocessor 21 controls the display module 109 of information output circuit 17 via data bus 23 and address bus 22 and controls the sound control circuit 110 by an I/O line 100. The display module 109 may be an intelligent LED display module PD3535, available from Siemens or a LCD graphics module available from Epson. The sound control circuit 110 may be a buzzer as shown in FIG. 9 or it may be an advanced speech synthesizer.

Referring now to FIG. 10, presented are the details of the power supply circuit used in the application system 11 of the present invention.

During operation of application system 11, power is derived from rechargeable battery 95 which may be, for example, a six volt rechargeable Ni—Cd battery, or the like. Battery 95 is connected through relay 99 to relay 98. The coil of relay 98 is powered by transistor 106 which is controlled by the output of NAND gate 102.

NAND gates 102, 103, 104 and 105 are configured to form a resettable latch. When on button 18 is depressed, the latch turns on transistor 106 which activates the coil of relay 98. When off button 19 is depressed, the latch is reset thus turning transistor 106 off, and removing power from the coil of relay 98. Microprocessor 21 may also reset the latch by pulling low momentarily on the Auto-Off line 107. This helps to save unnecessary power consumption when the system 11 is being left in an idle state.

When the coil of relay 98 is powered, battery 95 is connected to voltage regulator 97 which provides regulated voltage Vcc which is used to power various components of application system 11.

Connector 96 is provided to accommodate an external ac/dc adapter (not shown) which is used to charge battery 95. When an external dc adapter is connected to connector 96, voltage regulator 101 produces a regulated voltage which powers the coil of relay 99. This causes battery 95 to be disconnected from voltage regulator 97, and causes the output of voltage regulator 101 to be connected to the input of voltage regulator 97, thus permitting application system 11 to be powered by the external dc adapter. An indication of the existence of external dc voltage is applied to emission sensor 53 (FIG. 7) through EXT DC IN line 115.

If external dc power is connected (determined by emission sensor 53 when application system 11 is initially powered), microprocessor 21 executes the battery charging control routine, stops controllable generator 29 and disables the carrier oscillator 32. It also sends a signal to the battery charging control 57 and turns on the fast charging circuits. A message is displayed on display 17 or on a separate light emitting diode indicating that the battery is being charged.

During the battery charging routine, microprocessor 21 constantly monitors the battery voltage from the -dV detector 58 via data bus 23. Once the required -dV is detected, Ni—Cd battery 95 has reached its full charge condition, microprocessor switches off the fast charge circuit and automatically removes power from the system 11. -dV detector 58 may be configured, for example, including a MAX166 digital to analog converter available from Maxim Integrated Products, Inc.

The battery voltage is constantly monitored by the battery voltage monitor 108. Once the battery voltage drops to a predetermined low level (the voltage level at which the output emission power drops by 3% of the calibrated value), a signal is provided to microprocessor 21 which in turn stops the emission and provides an error message on the display 17. Battery voltage monitor 108 may be, for example, a voltage supervisory integrated circuit available from Texas Instruments or SGS Thompson.

Referring now to FIGS. 11a–d, presented are flow charts of the operation of the application system 11 of FIGS. 1 and 2, in accordance with the method of the present invention. In practice, the flowcharts of FIGS. 11a–d are encoded in an appropriate computer program and loaded into the operating program storage portion of microprocessor 21 in order to cause microprocessor 21 to control the function of application system 11.

Figure 11A:
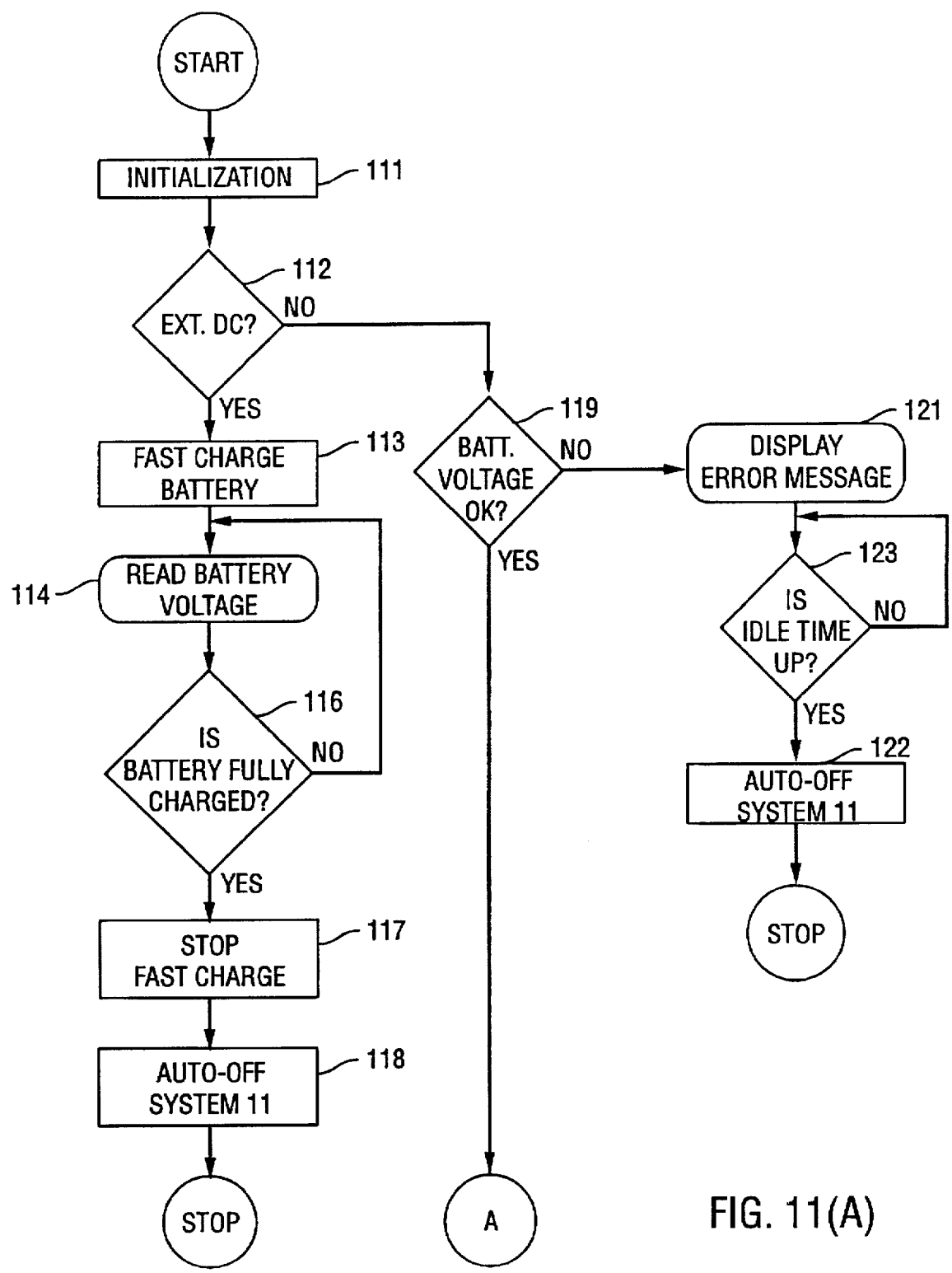
FIGS. 11a–e are flow charts of the method of operation of the system of FIG. 1 and 2, in accordance with the present invention.

Referring to FIG. 11a, microprocessor 21 starts execution of the program when switch 18 is activated. In block 111, microprocessor 21 initializes the circuits by stopping the wave form address generator 41, disabling the carrier oscillator 32 and displaying a welcome message to the user on display module 109.

In block 112, the source of dc power is immediately checked after initialization. If an external dc power source is connected, for example an ac/dc adapter, it is assumed that system 11 should function as a Ni—Cd battery charger. Microprocessor 21 passes control to block 113 which switches on the fast charge mode of the battery charging control 57 and monitors the battery voltage via the -dV detector 58 in the control loop including blocks 111 and 116. Once the Ni—Cd battery 95 reaches its full-charged state as detected by -dV detector 58, microprocessor 21 switches off the fast charging current in block 117 and automatically switches off system 11 in block 118.

If decision block 112 determines that external dc source is not connected, system 11 is powered by the internal battery 95. The battery voltage monitor 108 monitors the battery voltage at all times and provides information to microprocessor 21 for use in decision block 119. If the battery level drops to a predetermined low level, microprocessor 21 displays an error message on the display 109 in block 121. This is to inform the user to re-charge the battery before using the system again. It also switches off system 11 automatically in block 122 if there is no user response as determined by timing loop 123.

Figure 11B:
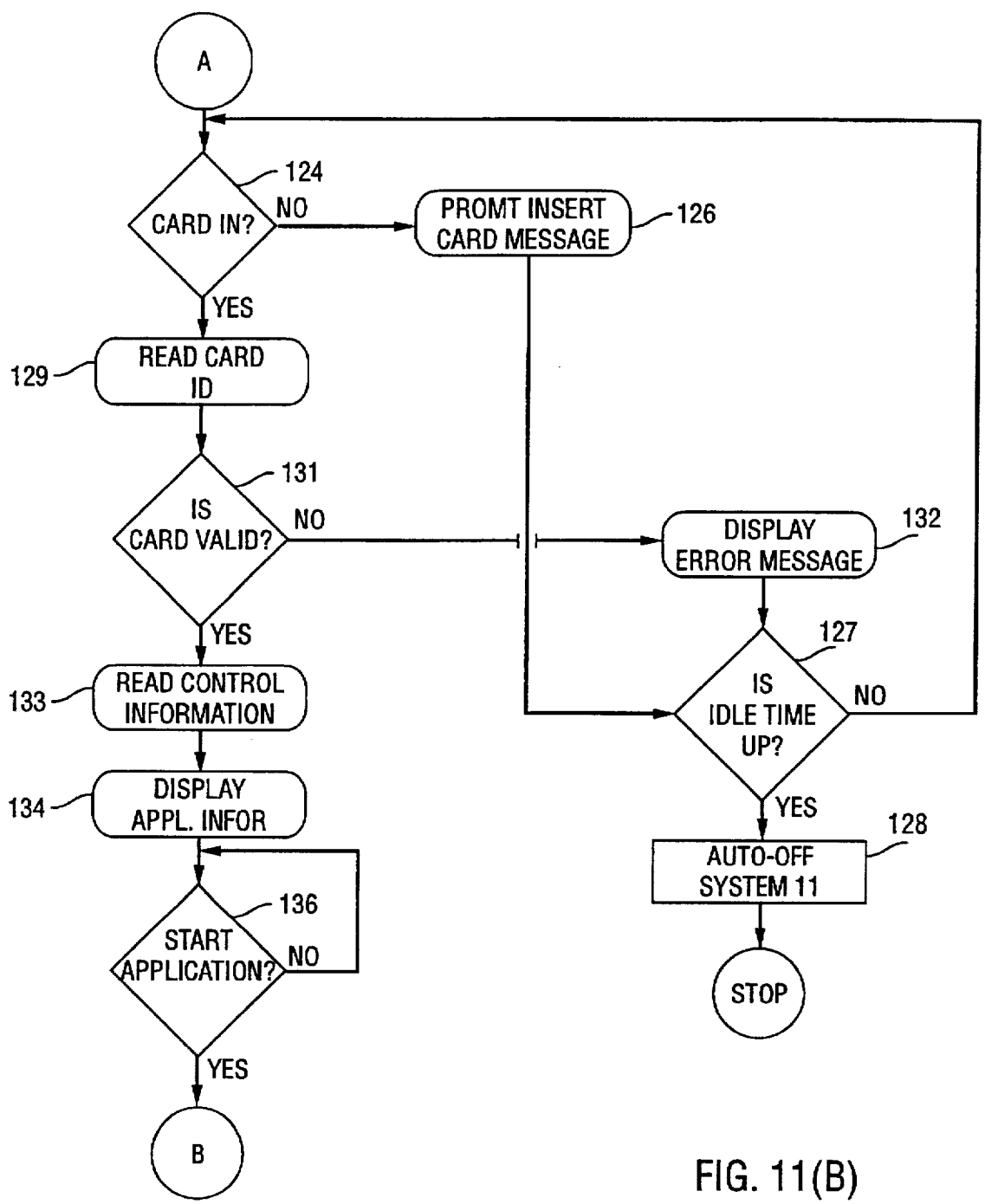

Referring now to FIG. 11b, after the battery level is checked, microprocessor 21 checks in block 124 if application storage device 52 is connected to system 11 via interface 16. If application storage device 52 is not connected, microprocessor 21 prompts for the application storage device 52 via information on display 109 in block 126. The application storage device 52 must be connected within a predetermined time limit as determined by block 127, or microprocessor 21 switches system 11 off in block 128.

Once block 124 determines that application storage device 52 is in place, microprocessor 21 reads an identification code in block 129 and checks if application storage device 52 is genuine and valid in block 131. If not, an error message is displayed in block 132 and system 11 is switched off after a predetermined time limit.

If a valid application storage device is connected, microprocessor 21 reads the control information in block 133 and stores the control information in the internal RAM area. Application information such as the type of treatment may be displayed on display 17 in block 134 for user re-confirmation. Microprocessor 21 then pauses and waits in block 136 for input from the user to start the application.

The user starts the application by pressing the on switch 18 again. Microprocessor 21 generates a test emission in block 137 by controlling the controllable generator 29 and prompts the user to check the emission with emission sensor 53 in block 138. Microprocessor 21 then checks the emission sensor input for the indicative signal in block 139. If the emission is not detected within a predetermined time limit as determined by block 142, microprocessor 21 displays a corresponding error message in block 143 and switches off system 11 in block 144 after a predetermined idle time as determined by block 146.

Figure 11C:
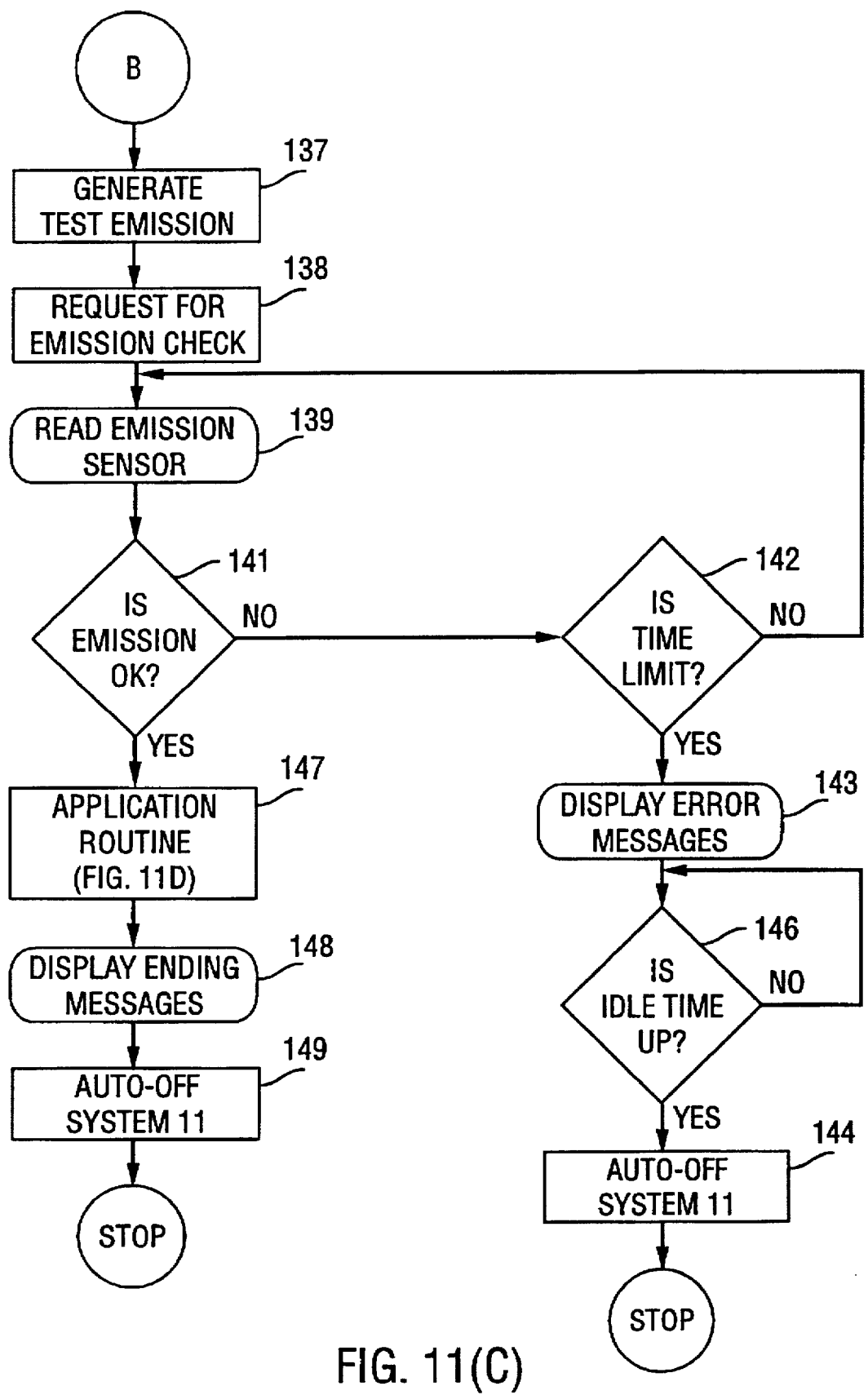
Figure 11D:
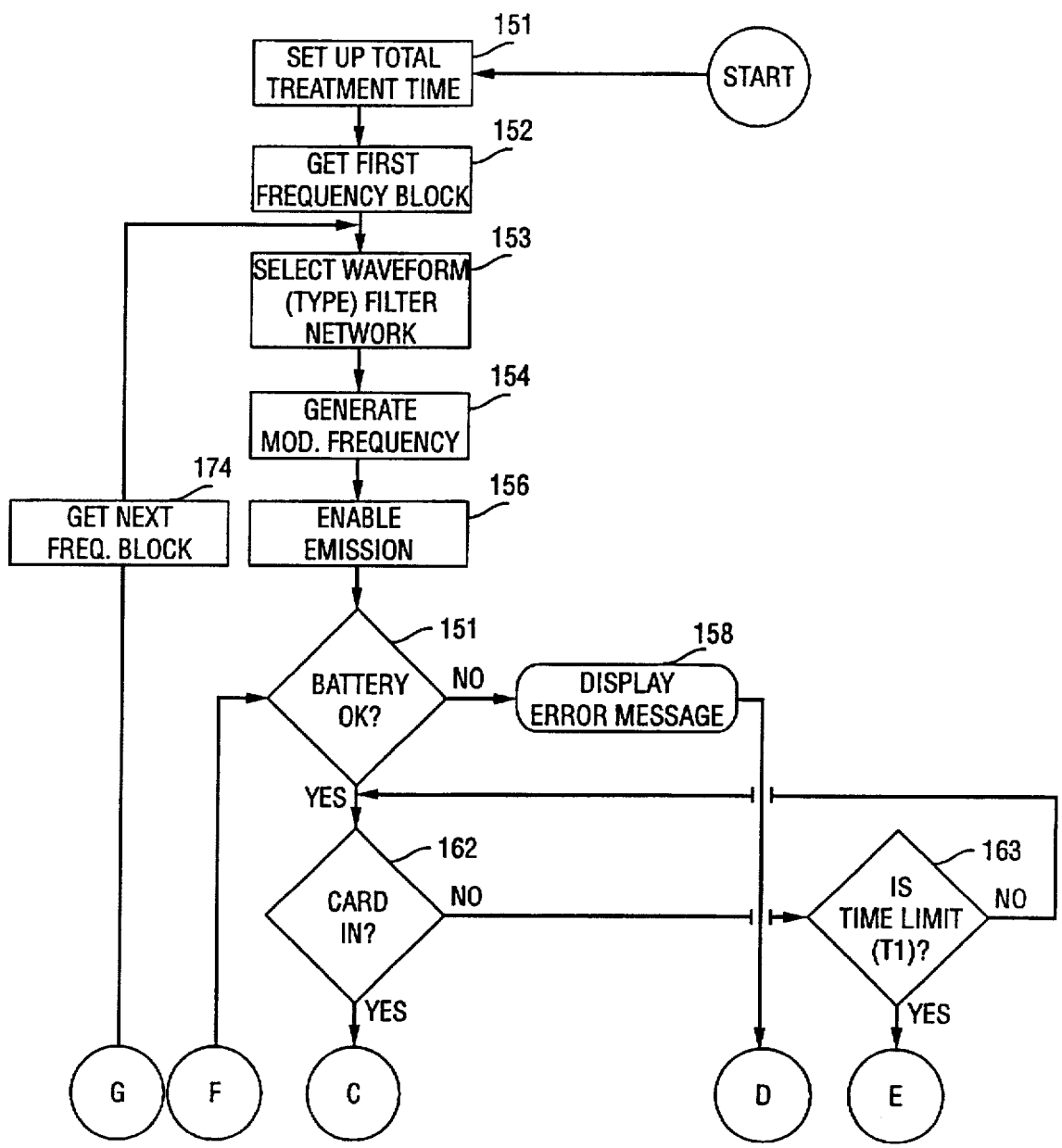
Figure 11E:
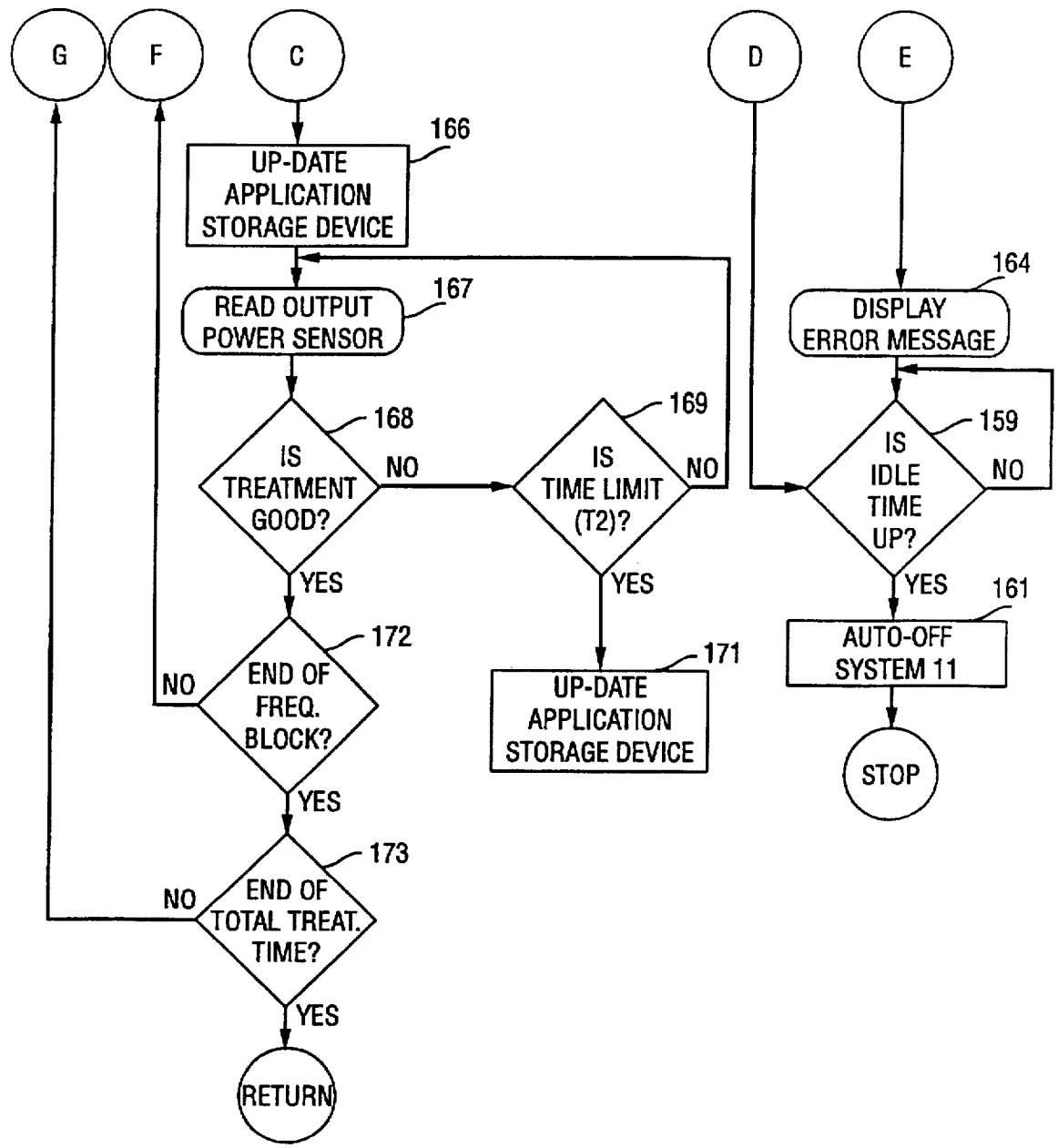

If the emission is detected within the predetermined time limit determined by block 142, control a passes to block 147 where microprocessor 21 executes the application software routine shown in detail in the flowchart of FIG. 11d.

The application software routine takes in the control information, interprets the information and controls the controllable generator 29 to generate the corresponding modulation wave form, frequency, power level, duration and duty cycle.

Referring to FIG. 11d, microprocessor 21 starts the routine by first setting up a total treatment time counter in block 151 which keeps tracks of the timing of the actual application. It then gets and interprets the first block of modulating frequency data in block 152. Then, in block 153 the modulation wave form is selected via extended I/O lines 45 and a suitable filter network is selected via the extended I/O lines 50. Also in block 153, the gain of modulation signal buffer amplifier 35 is adjusted in accordance with the power level control information. In block 154, the modulation frequency is controlled via the wave form address generator 41. The emission is then enabled by microprocessor 21 in block 156.

In decision block 157, the battery is checked using battery voltage monitor 108 to determine whether the battery level is acceptable. If not, control passes to block 158 where an appropriate error message is displayed. Then, system 11 is shut down in block 161 after a delay time determined by decision block 159.

If, on the other hand, the battery voltage is acceptable, control passes to decision block 162 where it is determined whether or not application storage device 52 is still inserted in interface 16. If not, control passes to decision block 163 where it is determined whether a predetermined time has expired without the presence of application storage device 52. When the time limit expires, control passes to block 164 where an appropriate error message is displayed, and eventually system 11 is automatically shut down in block 161.

If, on the other hand, decision block 162 determines that application storage device 52 is present within interface 16, control passes to block 166 where application storage device 52 is updated with user compliance information. Control then passes to block 167 where the output of power sensor 54 is read. Control then passes to block 168 where the output of power sensor 54 is assessed to determine a level of power being applied to the patient, and to assess whether or not treatment is being effectively applied. For example, if sensor 54 determines the presence of a large amount of reflected power, this condition may possibly be indicative of probe 13 not being properly connected or not being properly inserted into the mouth of a patient.

If decision block 168 determines that treatment is not being properly applied, control passes to decision block 169 which determines whether a predetermined time limit has been exceeded without detection of proper treatment. If the time limit is exceeded, control passes to block 171 where application storage device 52 is updated with information indicative of non-compliance with the treatment protocol.

If, on the other hand, decision block 168 determines that the treatment it is being properly applied, control passes to block 172 where it is determined whether the end of the particular modulation frequency block being applied has been reached. If not, control returns to decision block 157. If, on the other hand, decision block 172 determines that the end of the modulation frequency block presently being applied has been reached, Control passes to decision block 173 where it is determined whether the end of the treatment time has been reached. If so, control returns to block 148 (FIG. 11c). If, on the other hand, decision block 173 determines that the end of the treatment session has not been reached, control passes to block 174 where the next frequency block is read from application storage device 52, and control returns to block 153 for the continuation of the treatment session.

At the end of the application routine, control is returned and the microprocessor 21 displays an ending message in block 148 and switches system 11 off automatically in block 149.

FIGS. 12, 13, 14, 15, 16 and 17 present exemplary configurations for application storage device 52. It should be understood that other configurations for application storage device 52 are also possible, without departing from the spirit and the scope of the present invention.

Figure 12:
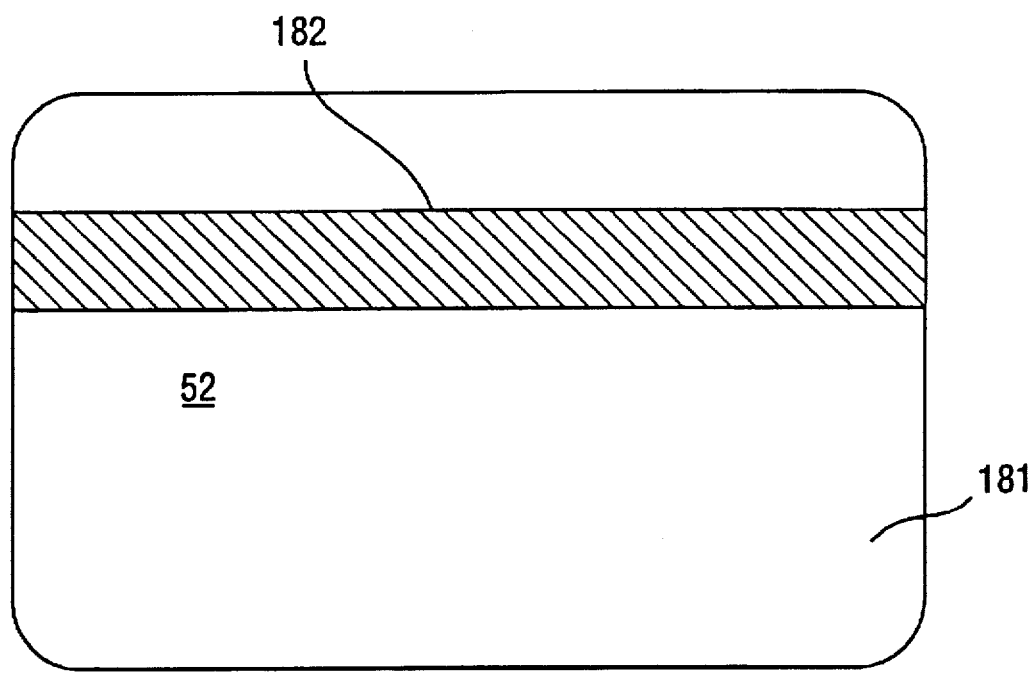
FIGS. 12, 13, 14, 15, 16 and 17 are examples of an application storage device for use with the present invention.

Referring to FIG. 12, application storage device 52 may comprise a magnetically encoded card 181 which includes a magnetically recordable portion 182 which stores the above-described control information and patient treatment compliance information.

Figure 13:
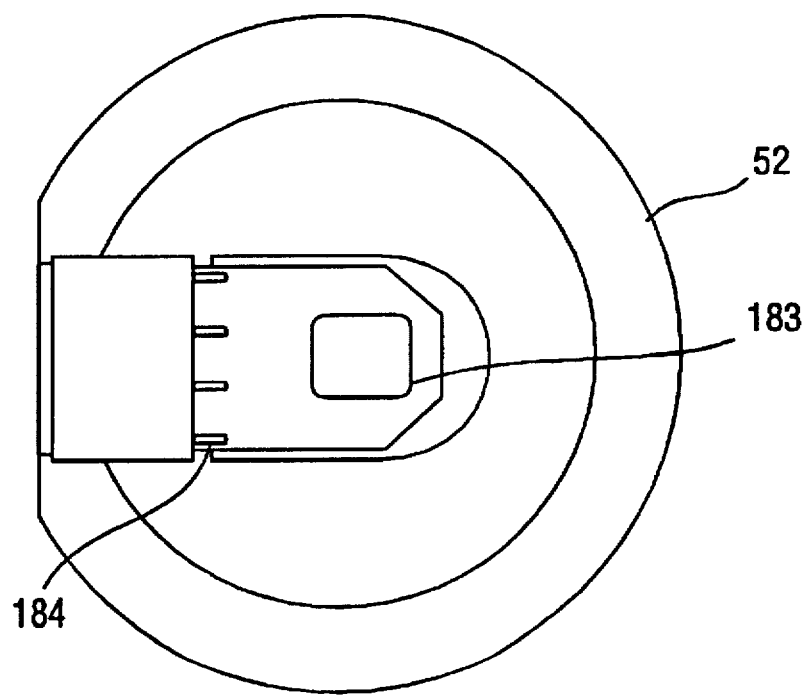

Referring to FIG. 13, application storage device 52 may comprise a semiconductor memory 183 which is connected through terminals 184 to interface 16. Semiconductor memory 183 is used to store the above described application control information and patient treatment compliance information.

Figure 14:
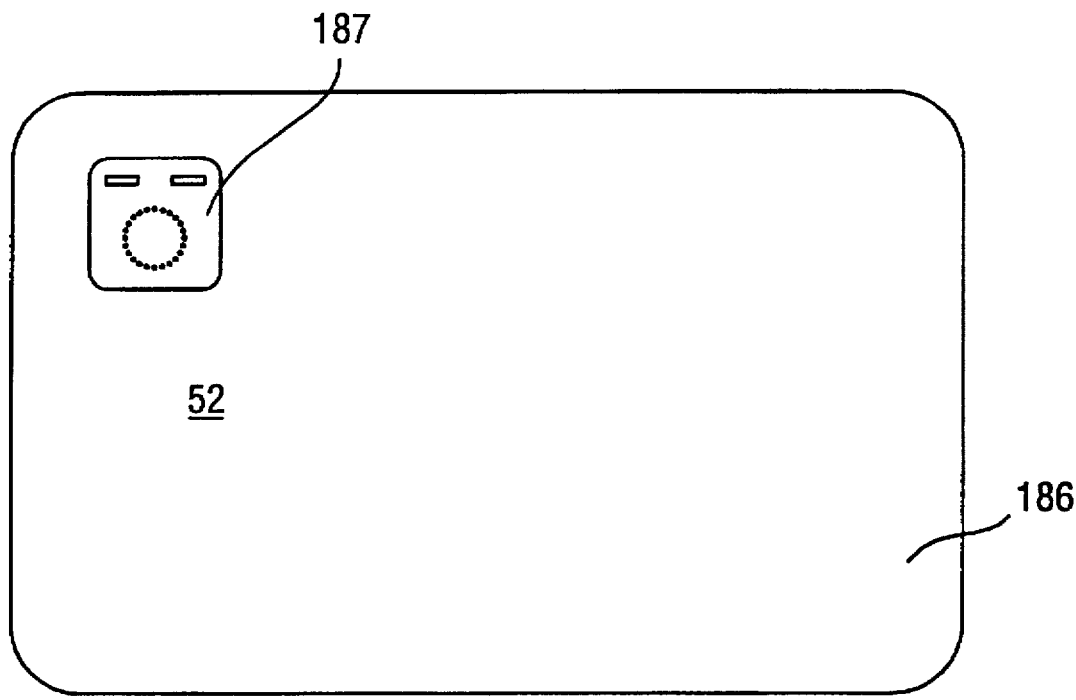

Referring now to FIG. 14, application storage device 52 may be in the form of a smart card 186 with the semiconductor hidden behind the contacts 187. The semiconductor may comprise only the memory with some security control logic, or may also include a stand-alone microprocessor that assists in communicating with the host microprocessor 21 via interface 16.

Figure 15:
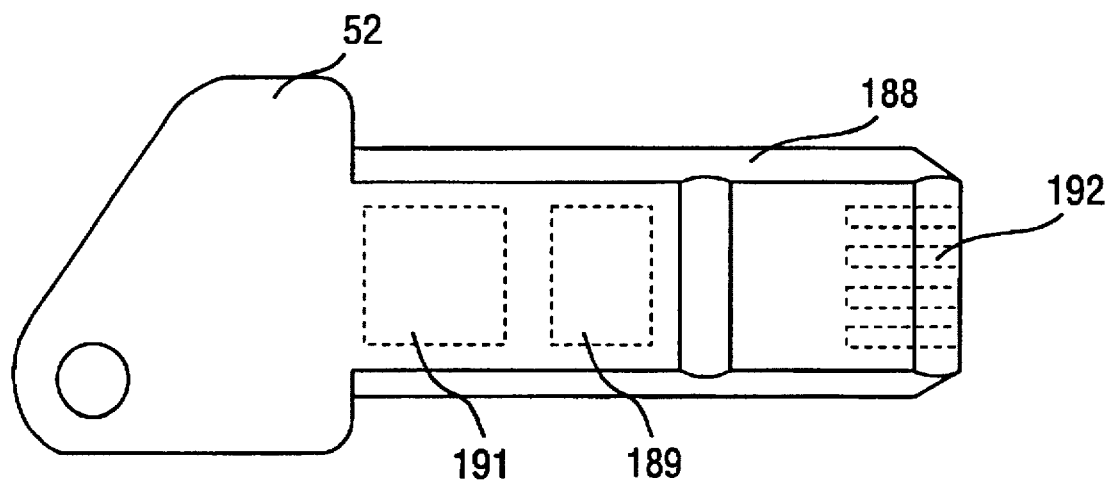

As shown in FIG. 15, application storage device 52 may take the form of a key-shaped structure 188 including semiconductor memory 189 and microprocessor 191 which are operatively connected to electrical terminals 192.

Figure 16:
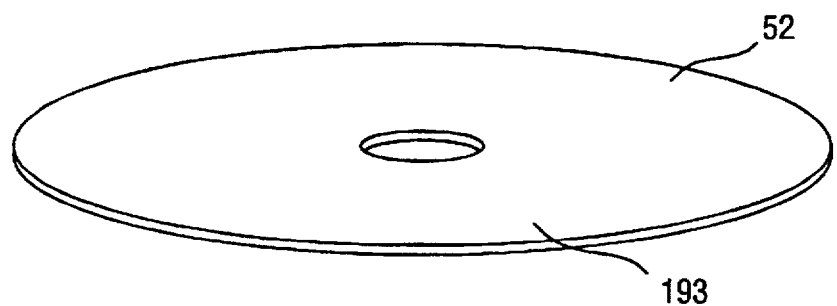

FIG. 16 illustrates application storage device 52 in the form of a compact disk read only memory (CDROM) 193, on which control information is optically encoded.

Figure 17:
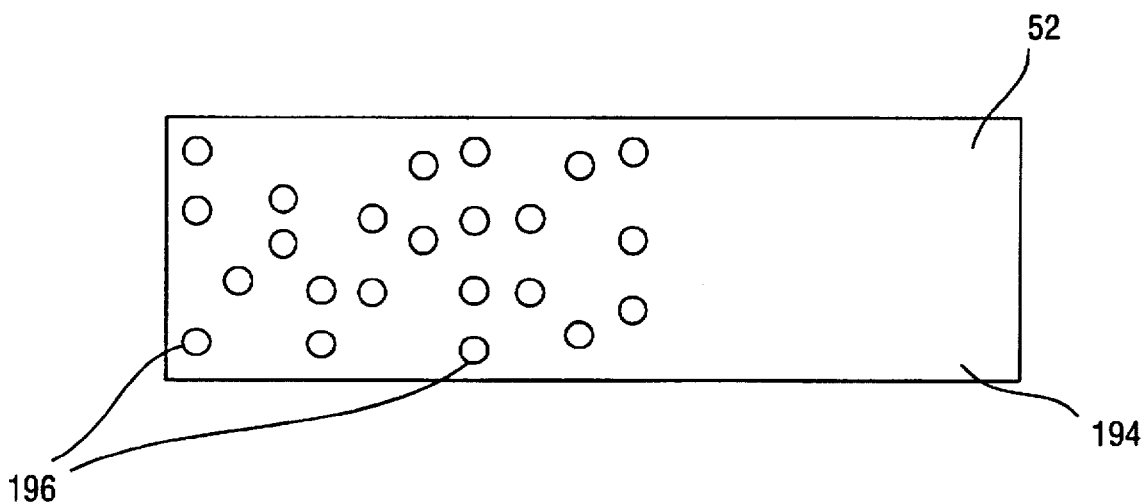

Finally, as shown in FIG. 17, application storage device 52 may take the form of a punched card 194, in which control information is tangibly embodied in a pattern of punched holes 196.

TREATMENT EXAMPLES

The system of the invention for applying a modulated low-energy electromagnetic emission to a patient, is useful for the treatment of a patient suffering from central nervous system (CNS) disorders. In use of the system, the probe for applying the modulated carrier signal to the patient is connected to the patient, in particular by means of a mouth piece probe placed in the patient's mouth and the modulated low-energy electromagnetic emission is applied to the patient through the probe. At least two low-energy electromagnetic emissions modulated at different frequencies are applied to the patient to achieve beneficial results. Beneficially, several discrete electromagnetic emissions modulated at different frequencies are applied to the patient for a specific treatment of a CNS disorder. The time of treatment, which relates to the amount of the low-energy electromagnetic emission applied to the patient, may vary between wide limits depending on the nature of the disorder being treated and the effect desired. However, in general, the time of treatment would be at least one minute per day and could continue over several hours per day, but would normally be at most one hour per day. Most preferably, the treatment time is at least ten minutes per day which may be divided up into two or more application times, e.g., of from five to forty-five minutes per application time.

EXAMPLE I: TREATMENT OF INSOMNIA

One of the specific CNS disorders which has been very satisfactorily treated with the aid of the system of the invention is sleep disorder, in particular insomnia which is the most important sleep disorder. Clinical insomnia is defined by the Diagnostic and Statistical Manual of Mental Disorders (DSM-III-R), from the American Psychiatric Association 1987 (DSM-III-R):

"Diagnostic criteria for Insomnia Disorders

A. The predominant complaint is of difficulty in initiating or maintaining sleep, or of non restorative sleep (sleep that is apparently adequate in amount, but leaves the person feeling unrested).

B. The disturbance in A occurs at least three times a week for at least one month and is sufficiently severe to result in either a complaint of significant daytime fatigue or the observation by others of some symptom that is attributable to the sleep disturbance, e.g., irritability or impaired daytime functioning.

C. Occurrence not exclusively during the course of "Sleep-Wake Schedule Disorder or a Parasomnia."

"Diagnostic criteria for 307.42 Primary Insomnia

Insomnia Disorder, as defined by criteria A, B and C above, that apparently is not maintained by any other mental disorder or any known organic factor, such as a physical disorder, a Psychoactive Substance Use Disorder, or a medication."

The frequencies of modulation for the low-energy electromagnetic emissions applied to the patient for treating insomnia have been found to be effective when comprising two or more frequency modulations selected from the following bandwidths: 1–5 Hz, 21–24 Hz, 40–50 Hz, 100–110 Hz, or 175–200 Hz.

A very specific example of a set of low-energy electromagnetic emissions applied to a patient suffering from insomnia are modulated at the following frequencies and applied sequentially to the patient for the times indicated over a period of 20 minutes per day, three times a week or every day is as follows:

Protocol P40: about 2.7 Hz for about 6 seconds, followed by about a 1 second pause, about 21.9 Hz for about 4 seconds, followed by about a 1 second pause, about 42.7 Hz for about 3 seconds, followed by about a 1 second pause, about 48.9 Hz for about 3 seconds, followed by about a 1 second pause.

A study employing the above protocol P40 set of frequency modulations and times of application was performed to test the efficacy of low-energy emission therapy (LEET) in the treatment of insomnia.

EXAMPLE IA: TREATMENT OF INSOMNIA

The primary endpoints of the study were defined as measures of sleep (total sleep time (TST) and sleep latency (SL)) as measured by polysomnography (PSG). Secondary endpoints (also quantified by PSG) included measures of rapid eye movement (REM), non-REM, number of awakenings after sleep onset, and wake after sleep onset (WASO). Additional measures of individual responses to treatment were derived from the patients' reports.

METHODS:

The study was a placebo-controlled, double-blind, repeated-measures study performed on a total of thirty subjects. Treatment was provided via a 12 V battery-powered device in accordance with the present invention, emanating the P40 protocol.

Forty-six subjects underwent polysomnographic (PSG) evaluation in order to yield the thirty subjects who participated in the study. The subjects who met the PSG criteria were randomized to treatment groups by means of a coin flip. All 30 subject completed the study. Subjects were identified for potential enrollment via television and radio advertisement.

Each study subject completed a number of rating scales prior to entry into and throughout the study. These scales included the Hamilton Anxiety Rating Scale (HARS), the Profile of Mood States reported sleep rating scale. The HARS, POMS, and HSCL were obtained during the initial psychiatric screening prior to entry, on a weekly basis thereafter, and at completion of the study. Daily sleep logs were maintained by patients throughout the study. Patients received treatment 3 times per week over the 4 weeks of the study, and were randomly assigned to either active or inactive treatment groups, under double-blind conditions. Treatment was performed with patients in a supine position, resting comfortably on a bed in a sleep-recording room with a low level of illumination.

ENTRY CRITERIA:

To qualify for a baseline PSG study, subjects were screened for chronic insomnia of a non-medical etiology. Patients with active medical illness, psychiatric diagnoses (DSM-III-R), alcohol/drug addiction, or active use of benzodiazepines and/or tranquilizers were excluded.

Entry into the study required patients to be suffering from chronic insomnia (more than six months) and to meet at least 2 of the 3 established PSG sleep criteria: sleep latency of greater than 30 minutes duration; total sleep time (TST) of less than 360 minutes per night; sleep efficiency (total sleep time/total recorded time) of less than 85%. Subjects were asked to go to bed in the laboratory at their regular bedtime and were allowed to sleep "ad libitum". The study was ended by the technician only if the time in bed was greater than 8.5 hours and the subject at that time was lying in bed awake.

STATISTICAL METHODS:

For purposes of statistical analysis, a Student's t-test was performed comparing the difference in the change scores (post pre) between the treatment groups. Where appropriate, analyses were adjusted for baseline values using linear regression.

RESULTS:

Base Line Evaluation

Of the 30 consenting, eligible patients, 15 were randomly assigned to each of the treatment groups. In the active treatment group, there were 4 men and 11 women (mean age of 39 years). I. the inactive treatment group there were 6 men and 7 women (mean age of 41 years). The mean age of the subjects did not differ significantly between groups.

At baseline, by definition, all patients met criteria for severe insomnia. Although the study groups had comparable patient reported TST durations at baseline, the placebo group had a significantly longer TST at baseline when measured by PSG. Both groups had prolonged sleep latency periods at baseline (>20 mins) as determined by both patient reported and PSG measures. Pre-treatment sleep parameters are summarized in Table II.

Post-Treatment Evaluation: Interval Changes

All 30 patients completed the trial. In the placebo group, the PSG TST decreases slightly at the conclusion of the study, compared with baseline values (from 337.0±57.2 to 326.0±130.5 TST change of −11.0±122.8, p=0.74). Similarly, the pre- and post-patient reported measures of TST were nearly identical in the placebo group (from 269.0±73.6 to 274.3±103.2, TST change of 5±122, p=0.87). In contrast, the PSG measured TST increased in the active group by nearly 90 minutes (from 265.9±67.5 to 355.8±103.5, TST increase of 89.9±93.9, p=0.002). This finding is consistent with the patient reported improvement reported by the active treatment group (from 221.7±112.3 to 304.0±144.7, TST increase of 82.3±169.0 minutes, p=0.08).

Also worth noting is that, while the proportion of REM sleep in the placebo group increased only slightly from 17.3 to 18.7% of total sleep time, in the active group, it increased from 16.3 to 20.9% of the total sleep time. The patient reported measure of sleep latency improved by more than 50% in the active treatment group during the study (from 145.8±133.2 to 70.7±67.9, p=0.03) while sleep latency increased slightly in the placebo group during the study period (from 71.3±41.2 to 82.8±84.8, p-0.58).

SIDE EFFECTS:

Side effects are summarized in Table I. One patient in the active treatment group reported increased dreaming. No other side effects were reported.

TABLE I

| SIDE EFFECTS | | |
|---|---|---|
| Side Effect | Active | Placebo |
| Mild Headache | 0 | 0 |
| Average Headache | 0 | 0 |
| Tingling Sensation | 0 | 0 |
| Worsening of Sleep | 0 | 0 |
| Nausea | 0 | 0 |
| Uncomfortable sensation in mouth | 0 | 0 |
| Fatigue | 0 | 0 |
| Fever | 0 | 0 |
| Increased Dreaming | 1 (3%) | 0 |
| Metallic Taste | 0 | 0 |
| Dizziness | 0 | 0 |
| Lightheadedness | 0 | 0 |

CONCLUSIONS:

Subjects enrolled in this study demonstrated severely disturbed sleep criteria by both patient reported and PSG measures. The active treatment group exhibited an improvement of 34% in PSG TST, while the placebo group demonstrated a 3% decrease in PSG TST. The significant difference in TST changes between groups from baseline was not explained solely by the significantly different baseline TST of the active and placebo groups. Adding the baseline TST in a regression model using treatment as a predictor did not adequately account for the difference in TST between the treatment groups.

Patient reported measurements confirmed the PSG findings, with a 37% improvement in the active group TST compared with a 2% improvements in the control group. Other PSG and patient reported measures of sleep indicated consistently greater improvement in the active group compared with the placebo group. Those results indicate that LEET therapy (using the P40 program) on an every-other-day basis, successfully treats insomnia by both lengthening the total duration of sleep and shortening sleep latency. Furthermore, patients felt that their sleep patterns were improved. Post-treatment sleep parameters are summarized in Table III.

TABLE II

PRE-TREATMENT SLEEP PARAMETERS
Values shown represent mean ± standard deviation.
Measurements are derived from 1 night PSG obtained prior to initiation of therapy.
PSG REPORT OF SLEEP:
PSG ANALYSIS
N = 15 per group

| | Active | Placebo | p = Value |
|---|---|---|---|
| Total Sleep Time (mins.) | 265.9 ± 67.5 | 337.0 ± 67.2 | 0.004 |
| Sleep Latency (mins.) | 63.9 ± 64.1 | 46.6 ± 45.3 | 0.400 |

TABLE III

POST-TREATMENT SLEEP PARAMETERS
Values shown represent mean ± standard deviation.
Interval changes are reported as PSG data obtained at the end of the study (day 28) - PSG data obtained prior to the initiation of treatment.

| PSG POST-TREATMENT SLEEP PARAMETERS (1 Month) N = 15 per group | | | |
|---|---|---|---|
| | Active | Placebo | p = Value |
| Total Sleep Time (mins.) | 355.8 ± 103.5 | 326.0 ± 130.5 | 0.494 |
| Change TST (mins) | 99.9 ± 93.9 | −11.0 ± 4122.8 | 0.017 |
| Sleep Latency (mins) | 23.1 ± 12.8 | 27.0 ± 18.9 | 0.520 |
| Change SL (mins) | −40.8 ± 57.8 | −19.8 ± 37.9 | 0.250 |

| PATIENT REPORTS OF SLEEP: SLEEP LATENCY (mins) N = 15 per group | | | | |
|---|---|---|---|---|
| | Pre | Post | Change | p = Value |
| Active | | | | |
| Mean | 145.8 | 70.7 | −75.0 | 0.307 |
| Standard Deviation | 133.2 | 67.9 | 121.0 | |
| Control | | | | |
| Mean | 71.3 | 62.8 | 11.5 | 0.5813 |
| Standard Deviation | 41.2 | 84.8 | 78.9 | |
| p = value | 0.055 | 0.670 | 0.028 | |

| PATIENT REPORTS OF SLEEP: TOTAL SLEEP TIME (mins) N = 15 per group | | | | |
|---|---|---|---|---|
| | Pre | Post | Change | p = Value |
| Active | | | | |
| Mean | 221.7 | 304.0 | 82.3 | 0.0804 |
| Standard Deviation | 112.3 | 144.7 | 169.2 | |
| Control | | | | |
| Mean | 269.0 | 274.3 | 5.3 | 0.8683 |
| Standard Deviation | 73.6 | 103.2 | 122.3 | |
| p = value | 0.183 | 0.523 | 0.164 | |

EXAMPLE IB: TREATMENT OF INSOMNIA

Another double blind, patient-reported study was also designed to test the efficiency of low-energy emission therapy (LEET) in the treatment of insomnia of non-medical etiology.

The primary PSG of the study was to detect differences between the treatment groups in perceived sleep measures (total sleep time and sleep latency), as reported by the subjects.

METHODS:

The study was preformed on a total of 30 subjects. Treatment was provided using the device of the present invention with the P40 protocol powered by a 12-volt battery. All patients completed all phases of the study. In the inactive treatment group there were 8 males and 7 females (mean age of 40 years). In the active treatment group there were 6 males and 9 females (mean age of 39 years). There were no significant differences in age between the active treatment and inactive treatment populations.

Each study subject completed a number of rating scales prior to entry into and throughout the study. These scales included the Hamilton Anxiety Rating Scale (HARS), the Profile of Mood States (POMS), the Hopkins Symptom Check List (HSCL), and a patient reported sleep rating scale. The HARS, POMAS, and HSCL were obtained during the initial psychiatric screening prior to entry, on a weekly basis thereafter, and at completion of the study. Daily patient reported sleep rating scales were maintained by patients throughout the study. Patients received treatment 3 times per week over the 4 weeks of the study and were randomly assigned to either active or inactive treatment groups, under double-blind conditions. Treatment was performed with patients in a supine position, resting comfortably on a bed in a sleep-recording room with a low level of illumination. Subjects continued to record sleep log data for two weeks after discontinuation of treatment.

ENTRY CRITERIA:

Patients between 20 and 50 years of age were recruited into the study. Entry into the study required patients to meet at least 2 of the 3 established sleep criteria: patient reported sleep latency of greater than 30 minutes; patient reported total sleep time of less than 360 minutes; and patient reported sleek efficiency of less than 85% (calculated as TST/total time in bed). Patients with active medical illnesses, psychiatric illnesses (according to DSM-III-R), drug or alcohol dependence were excluded.

STATISTICAL METHODS:

For the purposes of statistical analysis, a Student's t-test was performed comparing the difference of the change scores (post-pre) between each of the treatment groups.

RESULTS:

Throughout the course of the study, subjects were asked to estimate their total sleep time and sleep latency. A comparison was made between the patient reported sleep latency and the patient reported total sleep time at the time of the telephone interview, and the patient reported sleep latency and patient reported total sleep time obtained in the morning following the last night of treatment. A highly significant difference was seen for total sleep time (two-sided p=0.0021), with a more than threefold increase in the active group compared with the placebo group. The active treatment group also exhibited a >50% decrease in sleep latency as compared with the baseline. Patient reports of sleep are summarized in Table IV.

TABLE IV

PATIENT REPORTS OF SLEEP: SLEEP LATENCY AND TOTAL SLEEP TIME FOR STUDY

PATIENT REPORTED DATA: SLEEP LATENCY (mins) N = 15 per group

| | Pre | Post | Change | p = Value |
|---|---|---|---|---|
| Active | | | | |
| Mean | 53.8 | 25.1 | −28.7 | 0.0778 |
| Standard Deviation | 54.7 | 25.2 | 58.4 | |
| Control | | | | |
| Mean | 70.0 | 58.53 | −11.5 | 0.5710 |
| Standard Deviation | 67.0 | 71.0 | 77.0 | |
| p = value | 0.474 | 0.105 | 0.498 | |

TABLE IV-continued

PATIENT REPORTS OF SLEEP: SLEEP LATENCY AND TOTAL SLEEP TIME FOR STUDY

PATIENT REPORTED DATA: TOTAL SLEEP TIME (mins) N = 15 per group

| | Pre | Post | Change | p = Value |
|---|---|---|---|---|
| Active | | | | |
| Mean | 238.0 | 401.0 | 163.0 | 0.0001 |
| Standard Deviation | 58.3 | 80.8 | 87.0 | |
| Control | | | | |
| Mean | 264.0 | 315.5 | 51.5 | 0.0498 |
| Standard Deviation | 81.9 | 112.2 | 93.0 | |
| p = value | 0.325 | 0.024 | 0.002 | |

No statistically significant differences were seen between the two groups for any other measured parameter. There was no first or second night rebound insomnia as assessed by changes in either total sleep time or sleep latency. Furthermore, there is no evidence of rebound effect during the two weeks following discontinuation of treatment. Rebound insomnia analyses are summarized in Table V.

TABLE V

REBOUND INSOMNIA ANALYSIS FOR STUDY

FIRST DAY REBOUND INSOMNIA ANALYSIS OF STUDY
PRE = DAY 26
POST = 27
TOTAL SLEEP TIME (min)
N = 15 Per Group
N = 15 Control

| | Pre | Post | Change | p = Value |
|---|---|---|---|---|
| Active | | | | |
| Mean | 401.0 | 371.8 | −27.9 | 0.17 |
| Standard Deviation | 80.8 | 118.8 | 71.1 | |
| Control | | | | |
| Mean | 315.5 | 330.7 | 15.1 | 0.51 |
| Standard Deviation | 112.2 | 110.3 | 86.3 | |
| p = value | 0.024 | 0.34 | 0.16 | |

FIRST DAY REBOUND INSOMNIA ANALYSIS OF STUDY
PRE = DAY 26
POST = 27
TOTAL SLEEP TIME (min)
N = 15 Per Group
N = 15 Control

| | Pre | Post | Change | p = Value |
|---|---|---|---|---|
| Active | | | | |
| Mean | 25.1 | 32.5 | 5.7 | 0.15 |
| Standard Deviation | 25.1 | 32.1 | 13.8 | |
| Control | | | | |
| Mean | 58.5 | 51.2 | −7.3 | 0.72 |
| Standard Deviation | 71.1 | 52.6 | 76.1 | |
| p = value | 0.01 | 0.26 | 0.53 | |

*N = 14 for Active Day 27

TABLE V-continued

REBOUND INSOMNIA ANALYSIS FOR STUDY

SECOND DAY REBOUND INSOMNIA
ANALYSIS OF STUDY
PRE = DAY 26
POST = 28
TOTAL SLEEP TIME (min)
N = 15 Per Group
N = 15 Control

|  | Pre | Post | Change | p = Value |
|---|---|---|---|---|
| Active | | | | |
| Mean | 401.0 | 355.7 | −43.9 | 0.086 |
| Standard Deviation | 80.8 | 103.6 | 88.4 | |
| Control | | | | |
| Mean | 315.5 | 320.5 | 5.0 | 0.85 |
| Standard Deviation | 112.2 | 100.5 | 99.1 | |
| p = value | 0.024 | 0.36 | 0.17 | |

SECOND DAY REBOUND INSOMNIA
ANALYSIS OF STUDY
PRE = DAY 26
POST = 28
TOTAL SLEEP TIME (min)
N = 15 Per Group
N = 15 Control

|  | Pre | Post | Change | p = Value |
|---|---|---|---|---|
| Active | | | | |
| Mean | 25.1 | 41.4 | 14.6 | 0.098 |
| Standard Deviation | 25.1 | 39.8 | 30.8 | |
| Control | | | | |
| Mean | 59.5 | 75.25 | 16.7 | 0.44 |
| Standard Deviation | 71.1 | 82.4 | 81.7 | |
| p = value | 0.10 | 0.17 | 0.93 | |

N = 14 for Active Day 28

REBOUND INSOMNIA ANALYSIS OF STUDY
PRE = DAY 26
POST = DAY 40
TOTAL SLEEP TIME (min)
N = 15 Active
N = 15 Control

|  | Pre | Post | Change | p = Value |
|---|---|---|---|---|
| Active | | | | |
| Mean | 401.0 | 342.9 | −56.8 | 0.0094 |
| Standard Deviation | 80.8 | 91.0 | 69.7 | |
| Control | | | | |
| Mean | 315.5 | 323.7 | 8.1 | 0.68 |
| Standard Deviation | 112.2 | 79.0 | 74.4 | |
| p = value | 0.024 | 0.55 | 0.02 | |

REBOUND INSOMNIA ANALYSIS OF STUDY
PRE = DAY 26
POST = DAY 40
TOTAL SLEEP TIME (min)
N = 15 Active
N = 15 Control

|  | Pre | Post | Change | p = Value |
|---|---|---|---|---|
| Active | | | | |
| Mean | 25.1 | 32.0 | 5.2 | 0.55 |
| Standard Deviation | 25.1 | 41.9 | 32.1 | |
| Control | | | | |
| Mean | 58.6 | 32.0 | −26.5 | 0.11 |
| Standard Deviation | 71.1 | 28.9 | 59.9 | |
| p = value | 0.10 | 1.00 | 0.087 | |

N = 14 for Active Day 40

SIDE EFFECTS:

Side effects for the study are summarized in Table VI.

TABLE VI

SIDE EFFECTS DATA FOR STUDY
(N = 30)

| Side Effect | Active | Placebo |
|---|---|---|
| Mild Headache | 0 | 1 (3%) |
| Average Headache | 1 (3%) | 0 |
| Tingling Sensation | 0 | 0 |
| Worsening of Sleep | 0 | 0 |
| Nausea | 0 | 1 (3%) |
| Uncomfortable sensation in mouth | 0 | 0 |
| Fatigue | 0 | 0 |
| Fever | 0 | 0 |
| Increased Dreaming | 2 (6%) | 0 |
| Metallic Taste | 0 | 0 |
| Dizziness | 0 | 0 |
| Lightheadedness | 0 | 1 (3%) |

CONCLUSIONS:

Treatment with LEET using a battery powered system is highly effective in the treatment of insomnia, based on patient reported measurement of total sleep time.

PATIENT REPORTS OF SLEEP: Combined meta-analysis for the above two insomnia studies.

A meta-analysis of the patients' reports of sleep from the two studies is provided in Table VII. These studies were identical in terms of inclusion and exclusion criteria and study design (4-week, double-blinded, placebo-controlled). This analysis, performed on data from 60 patients (30 per group) demonstrates a 52 minute decrease in sleep latency, in the active group versus no change in the inactive group (p=0.025). Total sleep time increased by 128 minutes in the active group versus 28 minutes in the placebo (p=0.005).

TABLE VII

PATIENT REPORTS OF SLEEP:
SLEEP LATENCY AND TOTAL SLEEP TIME FOR
the Above Two Insomnia Studies PATIENT RESPONSE DATA:
SLEEP LATENCY (mins)
N = 30 Active

|  | Pre | Post | Change | p = Value |
|---|---|---|---|---|
| Active | | | | |
| Mean | 99.8 | 47.9 | −51.9 | 0.0062 |
| Standard Deviation | 110.4 | 55.4 | 96.2 | |
| Control | | | | |
| Mean | 70.7 | 70.7 | 0.0 | 0.9991 |
| Standard Deviation | 54.6 | 77.9 | 77.5 | |
| p = value | 0.203 | 0.199 | 0.025 | |

TABLE VII-continued

PATIENT REPORTS OF SLEEP:
SLEEP LATENCY AND TOTAL SLEEP TIME FOR
the Above Two Insomnia Studies PATIENT RESPONSE DATA:
TOTAL SLEEP TIME (mins)
N = 30 Active

|  | Pre | Post | Change | p = Value |
|---|---|---|---|---|
| Active | | | | |
| Mean | 229.8 | 352.5 | 122.7 | 0.0001 |
| Standard Deviation | 88.3 | 125.3 | 138.4 | |
| Control | | | | |
| Mean | 266.5 | 294.9 | 28.4 | 0.1648 |
| Standard Deviation | 76.8 | 108.0 | 109.3 | |
| p = value | 0.091 | 0.062 | 0.005 | |

EXAMPLE II: TREATMENT OF GENERALIZED ANXIETY DISORDER AND PANIC ATTACKS

As discussed above, several discreet electromagnetic emissions modulated at different frequencies are applied to a patient for a specific treatment of a CNS disorder. Based on the statistically significant improvements in total sleep time and sleep latency reported above, a low-energy emission therapy (LEET) program has been developed for a further CNS disorder, more closely defined as generalized anxiety disorders and panic attacks. For this indication, it has been determined that frequency modulations of the low-energy electromagnetic emissions should be within the following bandwidths: 1–5 Hz, 14–17 Hz, 40–50 Hz, and 175–200 Hz. More specifically, a variety of discreet modulations are selected from the above bandwidths and are applied for different times, one specific example comprising: about 1.4 Hz for about 40 seconds, about 2.8 Hz for about 20 seconds, about 3.4 Hz for about 15 seconds, and a separate group comprising: about 3.4 Hz for about 15 seconds, about 14.6 Hz for about 4 seconds, about 42.7 Hz for about 2 seconds, about 48.9 Hz for about 2 seconds, and about 189.7 Hz for about 1 second.

For example, the first group of frequencies mentioned may be applied to the patient sequentially for a period of about 15 minutes during the morning of each day of treatment, and the second group of frequencies may be applied to the patient sequentially for a period of about 30 minutes in the evening of each day of treatment.

Results obtained in treating patients suffering from anxiety and employing the above dosage criteria are reported below.

METHODS:

Subjects were recruited. After obtaining informed consent, subjects were interviewed with the Structured Clinical Interview for DSM-III-R Diagnosis (SCID), and symptoms were rated using structured interview versions of the Hamilton Anxiety Scale (Ham-A) (Hamilton, "The Assessment of Anxiety States by Rating,"*Br. J. Med. Phychol.*, 32:pp. 50–55, 1959), and the 31 item Hamilton Depression Rating Scale (Ham-D) (Hamilton, "A Rating Scale for Depression,"*J. Neurol. Neurosurg. Phychiat.*, 53:pp. 56–62, 1960). A physical examination was performed and blood was drawn from each patient for laboratory screening.

Subjects meeting the following requirements were entered into the study:

Inclusion criteria:
1. Age 18–65
2. Able to give informed consent
3. Meets DSM-III criteria for Generalized Anxiety Disorder or Adjustment Disorder with Anxious Mood for at least three months' duration.
4. Hamilton Anxiety Scale (HAM-A) equal or greater than 18

Exclusion criteria:
1. Meets DSM-III-R criteria for Substance Abuse in past three months.
2. Known contraindication to low intensity magnetic field (including pregnant patients or those planning to become pregnant in near future)
3. Meets DSM-III-R criteria for Current Mania, Hypomania, or Mixed-Episode Depression, Dysthymia, or Cyclothymia.
4. History of Panic Disorder, Obsessive Compulsive Disorder, Schizophrenia, or Schizoaffective Disorder
5. Acute suicidal ideation at screening interview
6. Use of anxiolytic medication within one week of screening visit
7. Dosage of other psychoactive agents not stable during preceding 12 weeks
8. Has started new psychotherapy in the preceding six months
9. Plans to begin new psychotherapy during the course of the study Subjects were given oral and written instructions for home use of the LEET device. Treatment consisted of daily exposures of 15 minutes each morning and 30 minutes each evening. The devices were pre-programmed to provide selected AM frequency RFEM waves via an antenna which the subject placed against the roof of their mouths. Subject were instructed to use the devices while recumbent with their eyes closed. All ratings were performed under open conditions. After six weeks of treatment, the devices were collected. Patients returned for follow-up visits in the second and fourth weeks after discontinuing treatment.

RESULTS:

Results are reported for the four women and six men who entered the protocol. As Table VIII illustrates, mean Ham-A improved from 23.4 to 8.1 after the first week of-treatment. By the third week of treatment, nine of the ten subjects showed improvement on the Ham-A of at least 50% of their baseline scores. Improvement was generally sustained through the sixth week. After discontinuation, the benefit of treatment appeared sustained in some subjects through the post-treatment follow-up. Although many subjects experienced some increase in Ham-A after discontinuing treatment, no subject reported rebound anxiety. Mean scores on Ham-D also improved from 15.01 at baseline and remained less than 6 after the first week of treatment.

TABLE VIII

| | MEAN HAMILTON ANXIETY SCALE SCORES, ALL SUBJECTS | | | | | | | |
|---|---|---|---|---|---|---|---|---|
| Baseline | Week 1 | Week 2 | Week 3 | Week 4 | Week 5 | Week 6 | Post Tx + 2 Wks | Post Tx + 4 Wks |
| 23.4 | 8.1 | 5.3 | 5.3 | 4.4 | 4.4 | 4.4 | 6.0 | 8.1 |

DISCUSSION:

The results are noteworthy for several reasons. First, LEET is an entirely new treatment paradigm which offers an attractive side effect profile and the potential to treat anxiety and related disorders. Second, the results are encouraging both in the magnitude of the effect and in the percentage of patients who achieved a clinically significant improvement. Third, the possibility that all instances of observed efficacy are due to placebo response is diminished by the duration of the observed improvement and that several of the patients had failed to improve in prior controlled studies and in previous open treatment with high potency benzodiazepines and/or antidepressants. Further research under double-blind conditions is indicated to further establish the efficacy of LEET and to clarify its role in clinical practice.

Although the invention has been described with reference to certain embodiments, it will be understood by those of skill in this art that additions, deletions and changes can be made to these embodiments, without departing from the spirit and scope of the present invention.

What is claimed is:

1. A program storage device readable by a machine having a carrier signal generator, a carrier signal modulator connected to said generator and a probe connected to said modulator, said program storage device tangibly embodying a program of instructions executable by the machine to perform the method steps of:

said carrier signal generator generating a radio frequency low energy carrier signal;

said carrier signal modulator modulating said radio frequency low energy carrier signal with a plurality of modulation signals to produce a modulated carrier signal; and applying said modulated carrier signal to a patient with said probe.

2. The program storage device claim 1, said modulating step comprising:

modulating said carrier signal with a first modulation signal for a first time increment; and modulating said carrier signal with a second modulation signal for a second time increment.

3. The program storage device of claim 2, wherein said second time increment occurs immediately after expiration of said first time increment.

4. The program storage device of claim 2, wherein the second time increment occurs after a delay for a third time increment after expiration of said first time increment.

5. The program storage device of claim 1, wherein said generating step comprises generating said radio frequency low energy carrier signal with spectral frequency components below 1 GHz, and wherein said modulating step comprises modulating the carrier signal with a plurality of modulation signals having spectral frequency components between 0.1 Hz and 10 kHz.

6. The program storage device of claim 5, wherein the carrier signal has spectral frequency components between 1 MHz and 900 MHz, and wherein the plurality of modulation signals have spectral frequency components between 1.0 Hz and 1000 Hz.

7. The program storage device of claim 5, wherein the plurality of modulation signals comprise frequency components selected from the bandwidths of 1-5 Hz, 9-12 Hz, 14-17 Hz, 21-24 Hz, 40-50 Hz, 100-110 Hz, and 175-200 Hz.

8. The program storage device of claim 5, wherein the plurality of modulation signals comprise frequency components selected from the bandwidths of 1-5 Hz, 14-17 Hz, 40-50 Hz, and 175-200 Hz.

9. The program storage device of claim 8, said modulating step comprising, modulating said carrier signal with a first group of modulation signals in conjunction with a second group of modulation signals.

10. The program storage device of claim 9, wherein the first group of modulation signals comprise frequency components selected from the bandwidth of 1-5 Hz.

11. The program storage device of claim 10, wherein said first group of modulation signals comprise frequency components selected from about 1.4 Hz, about 2.8 Hz, and about 3.4 Hz.

12. The program storage device of claim 11, said modulating step comprising, modulating said carrier signal with the following modulation signals for the following time increments: about 1.4 Hz for about 40 seconds, about 2.8 Hz for about 20 seconds and about 3.4 Hz for about 15 seconds.

13. The program storage device of claim 11, wherein the modulation signals are used to modulate said carrier signal sequentially over a period of about 15 minutes.

14. The program storage device of claim 11, said modulating step comprising, modulating said carrier signal with the following modulation signals for the following time increments: about 1.4 Hz for about 37 seconds, about 2.8 Hz for about 18 seconds and about 3.4 Hz for about 15 seconds.

15. The program storage device of claim 14, wherein the modulation signals are used to modulate said carrier signal sequentially over a period of about 15 minutes.

16. The program storage device of claim 10, wherein the second group of modulation signals comprise frequency components selected from the bandwidths of 1-5 Hz, 14-17 Hz, 40-50 Hz, and 175-200 Hz.

17. The program storage device of claim 16, wherein said second group of modulation signals comprise frequency components selected from about 3.4 Hz, about 14.6 Hz, about 42.7 Hz, about 48.9 Hz or about 189.7 Hz.

18. The program storage device of claim 17, said modulating step comprising, modulating said carrier signal with the following modulation signals for the following time increments: about 3.4 Hz for about 15 seconds, about 14.6 Hz for about 4 seconds, about 42.7 Hz for about 2 seconds, about 48.9 Hz for about 2 seconds, and about 189.7 Hz for about 1 second.

19. The program storage device of claim 18, wherein the modulation signals are used to modulate said carrier signal sequentially over a period of about 30 minutes.

20. The program storage device of claim 5, wherein the plurality of modulation signals comprise frequency components selected from the bandwidths 1-5 Hz, 21-24 Hz, and 40-50 Hz.

21. The program storage device of claim 20, wherein the plurality of modulation signals comprise frequency components selected from about 2.7 Hz, about 21.9 Hz, about 42.7 Hz, and about 48.9 Hz.

22. The program storage device of claim 21, said modulation step comprising, modulating said carrier signal with the following modulation signals for the following time increments: about 2.7 Hz for about 6 seconds, about 21.9 Hz for about 4 seconds, about 42.7 Hz for about 3 seconds, and about 48.9 Hz for about 3 seconds.

23. The program storage device of claim 22, wherein the modulation signals are used to modulate the carrier signal sequentially over a period of about 20 minutes.

24. The program storage device of claim 23, said modulating step further comprising, introducing a pause between application of the modulation signals.

25. The program storage device of claim 24, wherein the duration of the pause is about 1 second.

26. The program storage device of claim 1, said carrier signal modulator further controlling an amount of low energy emission applied to the patient.

27. The program storage device of claim 26, said controlling step comprising, controlling an amount of power applied to the patient to cause a specific absorption rate of energy absorbed by tissue of the patient to be from 100 microWatt to 50 Watts per kilogram of tissue.

28. The program storage device of claim 26, said tissue of the patient being central nervous system tissue.

29. The program storage device of claim 26, said controlling step comprising, controlling an amount of power applied to the patient to cause a specific absorption rate of energy absorbed by tissue of the patient to be from 100 microWatts to 10 Watts per kilogram of tissue.

30. The program storage device of claim 29, said tissue of the patient being central nervous system tissue.

31. The program storage device of claim 26, said controlling step comprising, controlling an amount of power applied to the patient to cause a specific absorption rate of energy absorbed by tissue of the patient to be from 1 milliWatt to 100 milliWatts per kilogram of tissue.

32. The program storage device of claim 31, said tissue of the patient being central nervous system tissue.

* * * * *

UNITED STATES PATENT AND TRADEMARK OFFICE
CERTIFICATE OF CORRECTION

PATENT NO.  :  5,634,939

DATED  :  June 3, 1997

INVENTOR(S)  :  Kuster et al.

It is certified that error appears in the above-identified patent and that said Letters Patent is hereby corrected as shown below:

```
In claim 13, column 26, line 35, delete "11" and insert --12--
therefor.
In claim 27, column 28, line 2, delete "100" and insert --1--
therefor.
In claim 28, column 28, line 4, delete "26" and insert --27--
therefor.
```

Signed and Sealed this

Twenty-sixth Day of August, 1997

Attest:

BRUCE LEHMAN

Attesting Officer      Commissioner of Patents and Trademarks